(12) United States Patent
Sicken et al.

(10) Patent No.: US 10,526,471 B2
(45) Date of Patent: Jan. 7, 2020

(54) PROCESS FOR PREPARING ETHYLENEDIALKYLPHOSPHINIC ACIDS, ESTERS AND SALTS AND USE THEREOF

(71) Applicant: CLARIANT PLASTICS & COATINGS LTD, Muttenz (CH)

(72) Inventors: Martin Sicken, Köln (DE); Fabian Schneider, Eppelheim (DE)

(73) Assignee: Clariant Plastics & Coatings Ltd, Muttenz (CH)

( * ) Notice: Subject to any disclaimer, the term of this patent is extended or adjusted under 35 U.S.C. 154(b) by 0 days.

(21) Appl. No.: 15/513,944

(22) PCT Filed: Sep. 10, 2015

(86) PCT No.: PCT/EP2015/070682
§ 371 (c)(1),
(2) Date: Mar. 23, 2017

(87) PCT Pub. No.: WO2016/045976
PCT Pub. Date: Mar. 31, 2016

(65) Prior Publication Data
US 2017/0267836 A1    Sep. 21, 2017

(30) Foreign Application Priority Data
Sep. 26, 2014  (DE) .......................... 10 2014 014 253

(51) Int. Cl.
| | | |
|---|---|---|
| C08K 5/5313 | (2006.01) |
| C07F 9/48 | (2006.01) |
| C07F 9/30 | (2006.01) |
| C09K 21/12 | (2006.01) |
| C07F 9/32 | (2006.01) |
| C07F 9/38 | (2006.01) |

(52) U.S. Cl.
CPC ............ C08K 5/5313 (2013.01); C07F 9/305 (2013.01); C07F 9/3264 (2013.01);
(Continued)

(58) Field of Classification Search
CPC ................................................... C08K 5/5313
See application file for complete search history.

(56) References Cited

U.S. PATENT DOCUMENTS

| | | | |
|---|---|---|---|
| 3,962,194 A | 6/1976 | Bollert et al. | |
| 4,001,352 A * | 1/1977 | Kleiner ................ | C07F 9/3235 |
| | | | 204/157.73 |

(Continued)

FOREIGN PATENT DOCUMENTS

| | | |
|---|---|---|
| CA | 1016185 A | 8/1977 |
| CN | 102164931 A | 8/2011 |

(Continued)

OTHER PUBLICATIONS

Mastalerz, "Synthesis of some ethylene-(P.P'-dialkyl)-diphosphinic acids as new potential antimetabolites of succinic acid", Roczniki Chemii, Ann. Soc. Chim. Polonorum, 38, 61-65 (1964).

(Continued)

Primary Examiner — Megan McCulley
(74) Attorney, Agent, or Firm — Morgan, Lewis & Bockius LLP

(57) ABSTRACT

The invention relates to the process for preparing ethylenedialkylphosphinic acids, esters and salts, wherein a) a phosphonic acid source (I) is reacted with olefins (IV) in the presence of a catalyst A to give an alkylphosphonous acid (II), or salt or ester thereof, b) the alkylphosphonous acid (II), or the salt or ester thereof, is reacted with an acetylenic compound (V) in the presence of a catalyst B to give the ethylenedialkylphosphinic acid derivative (III)

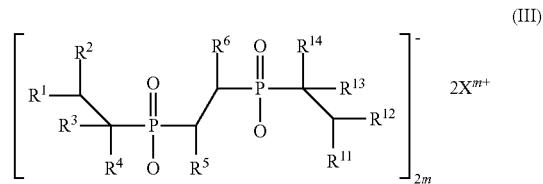

where $R^1$, $R^2$, $R^3$, $R^4$, $R^5$, $R^6$, $R^{11}$, $R^{12}$, $R^{13}$, $R^{14}$ are the same or different and are each independently H, $C_1$-$C_{18}$-alkyl, $C_6$-$C_{18}$-aryl, $C_6$-$C_{18}$-aralkyl, $C_6$-$C_{18}$-alkylaryl, where the $C_6$-$C_{18}$-aryl, $C_6$-$C_{18}$-aralkyl, $C_6$-$C_{18}$-alkylaryl groups may be substituted by —C(O)CH$_3$, OH, CH$_2$OH, NH$_2$, NO$_2$, OCH$_3$, SH and/or OC(O)CH$_3$, and X is Mg, Ca, Al, Sb, Sn, Ge, Ti, Fe, Zr, Zn, Ce, Bi, Sr, Mn, Cu, Ni, Li, Na, K, H and/or a protonated nitrogen base, and/or is H, $C_1$-$C_{18}$-alkyl, $C_6$-$C_{18}$-aryl, $C_6$-$C_{18}$-aralkyl, $C_6$-$C_{18}$-alkylaryl, (CH$_2$)$_k$OH, CH$_2$—CHOH—CH$_2$OH, (CH$_2$)$_k$O(CH$_2$)$_l$H, (CH$_2$)$_k$—CH(OH)—(CH$_2$)$_l$H, (CH$_2$—CH$_2$O)$_k$H, (CH$_2$—C[CH$_3$]HO)$_k$H, (CH$_2$—C[CH$_3$]HO)$_k$(CH$_2$—CH$_2$O)$_l$H, (CH$_2$—CH$_2$O)$_k$(CH$_2$—C[CH$_3$]HO)H, (CH$_2$—CH$_2$O)$_k$-alkyl, (CH$_2$—C[CH$_3$]HO)$_k$-alkyl, (CH$_2$—C[CH$_3$]HO)$_k$(CH$_2$—CH$_2$O)$_l$-alkyl, (CH$_2$—CH$_2$O)$_k$(CH$_2$—C[CH$_3$]HO)O-alkyl, (CH$_2$)$_k$NH$_2$, (CH$_2$)$_k$N[(CH$_2$)$_l$H]$_2$, where k and l are the same or different and are each independently an integer from 0 to 20, and m is 1 to 4, and the catalyst A comprises transition metals and/or transition metal compounds and/or catalyst systems composed of a transition metal and/or a transition metal compound and at least one ligand, and the catalyst B comprises electromagnetic radiation.

12 Claims, No Drawings

(52) U.S. Cl.
CPC .......... *C07F 9/3808* (2013.01); *C07F 9/4816* (2013.01); *C09K 21/12* (2013.01)

(56) References Cited

U.S. PATENT DOCUMENTS

| | | | | |
|---|---|---|---|---|
| 9,181,487 | B2* | 11/2015 | Hill | .......................... C07F 9/305 |
| 9,701,762 | B2 | 7/2017 | Nesvadba et al. | |
| 2011/0251312 | A1* | 10/2011 | Hill | .......................... C07F 9/305 524/126 |

FOREIGN PATENT DOCUMENTS

| | | |
|---|---|---|
| CN | 103724372 A | 4/2014 |
| DE | 2236037 A | 2/1974 |
| DE | 2302523 A1 | 8/1974 |
| DE | 19912920 A1 | 9/2000 |
| EP | 0699708 B1 | 3/1996 |
| JP | S49-101333 A | 9/1974 |
| JP | 2012-512213 A | 5/2012 |
| TW | 201425348 A | 7/2014 |
| WO | 2010/069545 A2 | 6/2010 |

OTHER PUBLICATIONS

International Search Report issued in corresponding International Patent Application No. PCT/EP2015/070682, dated Dec. 3, 2015.
International Preliminary Report on Patentability issued in corresponding International Patent Application No. PCT/EP2015/070682, dated Mar. 28, 2017.
Translation of Office Action issued in corresponding Taiwan Patent Application No. 104130156, dated Mar. 15, 2019.
Notification of the First Office Action issued in corresponding Chinese Patent Application No. 2015800512801, dated Jul. 26, 2018.
List of references cited in Japanese Office Action dated May 20, 2019.

* cited by examiner

PROCESS FOR PREPARING ETHYLENEDIALKYLPHOSPHINIC ACIDS, ESTERS AND SALTS AND USE THEREOF

The invention relates to a process for preparing ethylenedialkylphosphinic acids, esters and salts by means of at least one acetylenic compound and electromagnetic radiation. The invention also relates to the use of the ethylenedialkylphosphinic acids, esters and salts prepared by this process.

Ethylenediphosphinic acids and the esters and salts thereof are known compounds. Phosphinic acids of the H—P(O)(OX)—[CH$_2$CH$_2$—P(O)(OX)]$_n$H type with X=H, metal or an alkyl group and n greater than 1 are described in DE-A-19912920 and WO-GB-200100374. These phosphinic acids and their derivatives are oligomeric or polymeric. They are prepared by processes which give telomers but do not permit controlled access to phosphinic acids with specific chain length.

Organic phosphinic acids and salts and esters thereof are known as flame retardants. For instance, EP-B-0699708 describes flame-retardant polyester molding compositions, wherein the polyester molding compositions are rendered flame-retardant by the addition of calcium or aluminum salts of phosphinic acids or of diphosphinic acids. The aforementioned salts are obtained by reacting the appropriate phosphinic acids with calcium hydroxide or aluminum hydroxide.

Owing to their high phosphorus content and their bidentate nature, the diphosphinic acids are described as being very effective reactive flame retardants for polyesters, for example for textile applications. This is particularly true of ethylenebis(methylphosphinic acid), especially in the form of the glycol ester thereof (DE-A-2236037).

The preparation of the aforementioned ethylenebis(methylphosphinic acid) is technically very complex and is effected, for example, by an Arbuzov reaction of diisopropyl methylphosphonite, prepared from methylphosphonous dichloride by reaction with alcohols, with ethylene bromide [P. Mastalerz, Rocziniki Chem 38 (1964), pages 61-64] and subsequent ester cleavage.

DE-A-2302523 describes the reaction of alkylphosphonous esters with acetylene and the subsequent cleavage of the diester formed with hydrochloric acid to form alkyl chlorides. The alkylphosphonous esters used here are prepared from the corresponding phosphonous dihalides.

One disadvantage of the aforementioned processes is that they include the technically difficult cleavage of the corresponding esters as the last step, and can therefore be performed only with great difficulty. In addition, halogenated by-products are formed, which, like some of the aforementioned starting materials themselves too, are toxic, self-igniting and/or corrosive, i.e. are highly undesirable. Moreover, it is necessary to use halogenated reactants, but these should be avoided in many cases.

There has to date been a lack of processes for preparing ethylenedialkylphosphinic acids, esters and salts which are amenable to economically viable use on the industrial scale and which especially enable a high space-time yield.

There is also a lack of processes which are sufficiently effective without troublesome halogen compounds as reactants, and additionally of those in which the end products can be obtained and isolated readily, or else can be prepared in a controlled and desirable manner under controlled reaction conditions (for instance of a transesterification).

Furthermore, there is a lack of processes for preparing ethylenedialkylphosphinic acids, esters and salts which do not need a molecular, i.e. chemical, free-radical initiator. The free-radical initiators used to date have the disadvantage that they introduce usually troublesome secondary components and contaminants into the reaction, which subsequently have to be removed in a costly and inconvenient manner.

Secondary components of this kind are, for example, the decomposition products of the free-radical initiators, but also the solvents in which the free-radical initiators have been dissolved. Because the free-radical initiators are sometimes highly thermally unstable, handling on the production scale can be technically very complex and hence uneconomic and costly.

The aforementioned object is achieved by a process for preparing ethylenedialkylphosphinic acids, esters and salts, which comprises reacting a) a phosphinic acid source (I)

with olefins (IV)

in the presence of a catalyst A to give an alkylphosphonous acid (II), or salt or ester thereof,

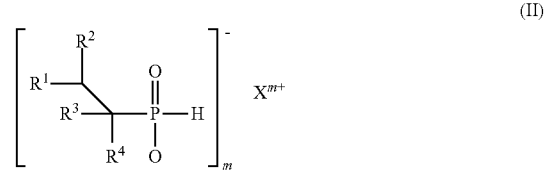

b) reacting the alkylphosphonous acid (II), or salt or ester thereof, thus formed with an acetylenic compound (V)

in the presence of a catalyst B to give the ethylenedialkylphosphinic acid derivative (III)

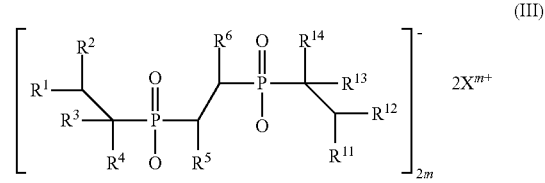

where
R$^1$, R$^2$, R$^3$, R$^4$, R$^5$, R$^6$, R$^{11}$, R$^{12}$, R$^{13}$, R$^{14}$ are the same or different and are each independently H, C$_1$-C$_{18}$-alkyl, C$_6$-C$_{18}$-aryl, C$_6$-C$_{18}$-aralkyl, C$_6$-C$_{18}$-alkylaryl, where the C$_6$-C$_{18}$-aryl, C$_6$-C$_{18}$-aralkyl, C$_6$-C$_{18}$-alkylaryl groups may be substituted by —C(O)CH$_3$, OH, CH$_2$OH, NH$_2$, NO$_2$, OCH$_3$, SH and/or OC(O)CH$_3$, and X is Mg, Ca, Al, Sb, Sn, Ge, Ti, Fe, Zr, Zn, Ce, Bi, Sr, Mn, Cu, Ni, Li, Na, K, H and/or a protonated nitrogen base, and/or is H, C$_1$-C$_{18}$-alkyl, C$_6$-C$_{18}$-aryl, C$_6$-C$_{18}$-aralkyl, C$_6$-C$_{18}$-alkylaryl, (CH$_2$)$_k$OH, CH$_2$—CHOH—CH$_2$OH, (CH$_2$)$_k$O(CH$_2$)$_l$H, (CH$_2$)$_k$—CH(OH)—(CH$_2$)$_l$H, (CH$_2$—CH$_2$O)$_k$H, (CH$_2$—C[CH$_3$]HO)$_k$H, (CH$_2$—C[CH$_3$]HO)$_k$(CH$_2$—CH$_2$O)$_l$H, (CH$_2$—CH$_2$O)$_k$(CH$_2$—C[CH$_3$]HO)H, (CH$_2$—CH$_2$O)$_k$-alkyl, (CH$_2$—C[CH$_3$]HO)$_k$-alkyl, (CH$_2$—C[CH$_3$]HO)$_k$(CH$_2$—CH$_2$O)$_l$-alkyl, (CH$_2$—CH$_2$O)$_k$(CH$_2$—C[CH$_3$]HO)O-alkyl, (CH$_2$)$_k$NH$_2$, (CH$_2$)$_k$N[(CH$_2$)$_l$H]$_2$, where k and l are the same or different and are each independently an integer from 0 to 20, and m is 1 to 4, and the catalyst A comprises transition metals and/or transition metal compounds and/or catalyst systems composed of a transition metal and/or a transition metal compound and at least one ligand, and the catalyst B comprises electromagnetic radiation.

Preferably, the process is executed in such a way that the alkylphosphonous acid (II), or salt or ester thereof, obtained after step a) is esterified with an alkene oxide or an alcohol M-OH and/or M'—OH, and the alkylphosphonous ester (II) and/or ethylenedialkylphosphinic ester (III) formed in each case is subjected to the further reaction step b).

Preferably, the ethylenedialkylphosphinic acid (III), or salt or ester thereof, obtained after step b) is also esterified with an alkene oxide or an alcohol M-OH and/or M'—OH.

Preferably, the ethylenedialkylphosphinic acid (III), or salt or ester thereof, obtained after step b) is subsequently reacted, in a step c), with metal compounds of Mg, Ca, Al, Sb, Sn, Ge, Ti, Fe, Zr, Zn, Ce, Bi, Sr, Mn, Li, Na, K and/or a protonated nitrogen base to give the corresponding ethylenedialkylphosphinic salts (III) of these metals and/or of a nitrogen compound.

Preferably, R$^1$, R$^2$, R$^3$, R$^4$, R$^5$, R$^6$, R$^{11}$, R$^{12}$, R$^{13}$, R$^{14}$ are the same or different and are each independently H, methyl, ethyl, n-propyl, isopropyl, n-butyl, isobutyl, tert-butyl and/or phenyl.

Preferably, X is H, Ca, Mg, Al, Zn, Ti, Mg, Ce, Fe, methyl, ethyl, n-propyl, isopropyl, n-butyl, isobutyl, tert-butyl, phenyl, oxyethylene, poly(oxyethylene), oxypropylene, poly(oxypropylene), oxybutylene, poly(oxybutylene) and/or allyl ether.

Preferably, the transition metals are rhodium, nickel, palladium, platinum and/or ruthenium.

Preferably, olefins used are gaseous olefins.

Preferably, the gaseous olefins are ethylene, propylene, 1-butene, 2-butene and/or 2-methylpropylene.

Preferably, the temperature in reaction step a) is 40-120° C. and that in reaction step b) is 30-100° C.

More preferably, the temperature in reaction step a) is 60-100° C. and that in reaction step b) is 50-80° C.

Preferably, the pressure in each of reaction step a) and reaction step b) is 0-10 bar.

Preferably, the pressure in each of reaction step a) and reaction step b) is 1-5 bar and the gas flow rate in each of reaction step a) and reaction step b) is 5-12 L/h.

Preferably, the electromagnetic radiation is UV radiation.

Preferably, the electromagnetic radiation is UV radiation having a wavelength between 400 and 10 nm.

Preferably, the acetylenic compound (V) is acetylene, methylacetylene, 1-butyne, 1-hexyne, 2-hexyne, 1-octyne, 4-octyne, 1-butyn-4-ol, 2-butyn-1-ol, 3-butyn-1-ol, 5-hexyn-1-ol, 1-octyn-3-ol, 1-pentyne, phenylacetylene and/or trimethylsilylacetylene.

More preferably, the acetylenic compound (V) is acetylene.

Preferably, the alcohol M—OH comprises linear or branched, saturated and unsaturated, monohydric alcohols and the alcohol M'—OH comprises polyhydric organic alcohols each having a carbon chain length of C$_1$-C$_{18}$.

The invention also relates to a method of using ethylenedialkylphosphinic acids, esters and salts prepared as described herein as an intermediate for further syntheses, as a binder, as a crosslinker or accelerator in the curing of epoxy resins, polyurethanes and unsaturated polyester resins, as polymer stabilizers, as crop protection agents, as a sequestrant, as a mineral oil additive, as an anticorrosive, in washing and cleaning composition applications and in electronics applications; as flame retardants, as flame retardants for clearcoats and intumescent coatings, as flame retardants for wood and other cellulosic products, as a reactive and/or nonreactive flame retardant for polymers, for production of flame-retardant polymer molding compositions, for production of flame-retardant polymer moldings, and/or for rendering pure and blended polyester and cellulose fabrics flame-retardant by impregnation; as flame retardants in the production or curing of epoxy resins, polyurethanes and unsaturated polyester resins for electronics applications.

The invention also relates to flame-retardant thermoplastic or thermoset polymer molding compositions, moldings, films, filaments and fibers comprising 0.5% to 45% by weight of ethylenedialkylphosphinic acids, salts or esters which have been prepared as described herein, 0.5% to 99.5% by weight of thermoplastic or thermoset polymer or mixtures thereof, 0% to 55% by weight of additives and 0% to 55% by weight of filler or reinforcing materials, where the sum of the components is 100% by weight.

Preferably, the aforementioned epoxy resins, polyurethanes and unsaturated polyester resins may further comprise hardeners, UV stabilizers, flexibilizers and/or other additions.

Preferably, the C$_6$-C$_{18}$-aryl, C$_6$-C$_{18}$-aralkyl and C$_6$-C$_{18}$-alkylaryl groups are substituted by SO$_3$X$_2$, —C(O)CH$_3$, OH, CH$_2$OH, CH$_3$SO$_3$X$_2$, PO$_3$X$_2$, NH$_2$, NO$_2$, OCH$_3$, SH and/or OC(O)CH$_3$.

Preferably, k=1 to 10 and l=1-10.

Preferably, the catalyst system A is formed by reaction of a transition metal and/or a transition metal compound and at least one ligand.

Preferably, the UV radiation is electromagnetic radiation within the wavelength range from 10 nm to 400 nm. This can be produced, for example, by a mercury vapor lamp.

All the aforementioned reactions can also be executed stepwise; it is likewise also possible to use the respective resulting reaction solutions in the different process steps.

Preferably, R$^{11}$=R$^1$, R$^{12}$=R$^2$, R$^{13}$=R$^3$ and R$^{14}$=R$^4$.

If the ethylenedialkylphosphinic acid (III) after step c) is an ester, it is possible with preference to conduct an acidic or basic hydrolysis in order to obtain the free ethylenedialkylphosphinic acid or salt thereof.

Preferably, the ethylenedialkylphosphinic acid is ethylenebis(octylphosphinic acid), ethylenebis(ethylphosphinic acid), ethylenebis(propylphosphinic acid), ethylenebis(i-propylphosphinic acid), ethylenebis(butylphosphinic acid), ethylenebis(sec-propyl-phosphinic acid), ethylenebis(i-butylphosphinic acid), ethylenebis(hexylphosphinic acid), ethylenebis(2-phenylethylphosphinic acid).

Preferably, the ethylenedialkylphosphinic ester is a propionic acid, methyl, ethyl; i-propyl; butyl, phenyl; 2-hydroxyethyl, 2-hydroxypropyl, 3-hydroxypropyl, 4-hydroxybutyl and/or 2,3-dihydroxypropyl ester of the abovementioned ethylenedialkylphosphinic acids.

Preferably, the ethylenedialkylphosphinic salt is an aluminium(III), calcium(II), magnesium(II), cerium(III), Ti(IV) and/or zinc(II) salt of the abovementioned ethylenedialkylphosphinic acids.

Compounds of the invention are especially those of the formula Y—P(O)(OX)—[CH$_2$CH$_2$—P(O)(OX)]$_n$Y in which, in each case, Y is ethyl and X is H;
Y is ethyl and X is Na;
Y is ethyl and X is butyl;
Y is ethyl and X is aluminum;
Y is butyl and X is H;
Y is butyl and X is Na;
Y is butyl and X is butyl;
Y is butyl and X is aluminum.

Preferably, the transition metals for the catalyst A are rhodium, nickel, palladium, platinum and/or ruthenium. These metals are likewise used for the transition metal compounds.

Preferred sources of the transition metals and transition metal compounds are their metal salts. Suitable salts are those of mineral acids containing the anions fluoride, chloride, bromide, iodide, fluorate, chlorate, bromate, iodate, fluorite, chlorite, bromite, iodite, hypofluorite, hypochlorite, hypobromite, hypoiodite, perfluorate, perchlorate, perbromate, periodate, cyanide, cyanate, nitrate, nitride, nitrite, oxide, hydroxide, borate, sulfate, sulfite, sulfide, persulfate, thiosulfate, sulfamate, phosphate, phosphite, hypophosphite, phosphide, carbonate and sulfonate, for example methanesulfonate, chlorosulfonate, fluorosulfonate, trifluoromethanesulfonate, benzenesulfonate, naphthylsulfonate, toluenesulfonate, t-butylsulfonate, 2-hydroxypropanesulfonate and sulfonated ion exchange resins; and/or organic salts, for example acetylacetonates and salts of a carboxylic acid having up to 20 carbon atoms, for example formate, acetate, propionate, butyrate, oxalate, stearate and citrate including halogenated carboxylic acids having up to 20 carbon atoms, for instance trifluoroacetate, trichloroacetate.

A further source of the transition metals and transition metal compounds is salts of the transition metals with tetraphenylborate anions and halogenated tetraphenylborate anions, for example perfluorophenylborate.

Suitable salts similarly include double salts and complex salts consisting of one or more transition metal ions and independently one or more alkali metal, alkaline earth metal, ammonium, organic ammonium, phosphonium and organic phosphonium ions and independently one or more of the abovementioned anions. Examples of suitable double salts are ammonium hexachloropalladate and ammonium tetrachloropalladate.

Preferred sources of the transition metals are the transition metal as an element and/or a transition metal compound in its zero-valent state.

Preferably, the transition metal is used in metallic form, or as an alloy with further metals, in which case boron, zirconium, tantalum, tungsten, rhenium, cobalt, iridium, nickel, palladium, platinum and/or gold is preferred here. The transition metal content in the alloy used is preferably 45%-99.95% by weight.

Preferably, the transition metal is used in microdisperse form (particle size 0.1 mm-100 µm).

Preferably, the transition metal is used supported on a metal oxide, for instance alumina, silica, titanium dioxide, zirconium dioxide, zinc oxide, nickel oxide, vanadium oxide, chromium oxide, magnesium oxide, Celite®, kieselguhr, on a metal carbonate, for instance barium carbonate, calcium carbonate, strontium carbonate, on a metal sulfate, for instance barium sulfate, calcium sulfate, strontium sulfate, on a metal phosphate, for instance aluminum phosphate, vanadium phosphate, on a metal carbide, for instance silicone carbide, on a metal aluminate, for instance calcium aluminate, on a metal silicate, for instance aluminum silicate, chalks, zeolites, bentonite, montmorillonite, hectorite, on functionalized silicates, functionalized silica gels, for instance SiliaBond®, QuadraSil™, on functionalized polysiloxanes, for instance Deloxan®, on a metal nitride, on carbon, activated carbon, mullite, bauxite, antimonite, scheelite, perovskite, hydrotalcite, heteropolyanions, on functionalized and unfunctionalized cellulose, chitosan, keratin, heteropolyanions, on ion exchangers, for instance Amberlite™, Amberjet™, Ambersep™, Dowex®, Lewatit®, ScavNet®, on functionalized polymers, for instance Chelex®, QuadraPure™, Smopex®, PolyOrgs®, on polymer-bound phosphines, phosphine oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silica and/or dendrimers.

Suitable sources for the metal salts and/or transition metals likewise preferably include their complex compounds. Complex compounds of the metal salts and/or transition metals are composed of the metal salts/transition metals and one or more complexing agents. Suitable complexing agents include for example olefins, diolefins, nitriles, dinitriles, carbon monoxide, phosphines, diphosphines, phosphites, diphosphites, dibenzylideneacetone, cyclopentadienyl, indenyl or styrene. Suitable complex compounds of the metal salts and/or transition metals may be supported on the abovementioned support materials.

The proportion in which the supported transition metals mentioned are present is preferably in the range from 0.01% to 20% by weight, more preferably from 0.1% to 10% by weight and even more preferably from 0.2% to 5% by weight, based on the total mass of the support material.

Suitable sources for transition metals and transition metal compounds include for example palladium, platinum, nickel, rhodium itself; palladium, platinum, nickel or rhodium, on alumina, on silica, on barium carbonate, on barium sulfate, on calcium carbonate, on strontium carbonate, on carbon, on activated carbon; platinum-palladium-gold alloy, aluminum-nickel alloy, iron-nickel alloy, lanthanoid-nickel alloy, zirconium-nickel alloy, platinum-iridium alloy, platinum-rhodium alloy; Raney® nickel, nickel-zinc-iron oxide; palladium(II) chloride, palladium(II) bromide, palladium(II) iodide, palladium(II) fluoride, palladium(II) hydride, palladium(II) oxide, palladium(II) peroxide, palladium(II) cyanide, palladium(II) sulfate, palladium(II) nitrate, palladium (II) phosphide, palladium(II) boride, palladium(II) chromium oxide, palladium(II) cobalt oxide, palladium(II) carbonate hydroxide, palladium(II) cyclohexane butyrate, palladium(II) hydroxide, palladium(II) molybdate, palladium(II) octanoate, palladium(II) oxalate, palladium(II) perchlorate, palladium(II) phthalocyanine, palladium(II) 5,9,14,18,23,27,32,36-octabutoxy-2,3-naphthalocyanine, palladium(II) sulfamate, palladium(II) perchlorate, palladium(II) thiocyanate, palladium(II) bis(2,2,6,6-tetramethyl-3,5-heptanedionate), palladium(II) propionate, palladium(II) acetate, palladium(II) stearate, palladium(II) 2-ethylhexanoate, palladium(II) acetylacetonate, palladium(II) hexafluoroacetylacetonate, palladium(II) tetrafluoroborate, palladium(II) thiosulfate, palladium(II) trifluoroacetate, palladium(II) phthalocyaninetetrasulfonic acid tetrasodium salt, palladium(II) methyl, palladium(II) cyclopentadienyl, palladium(II) methylcyclopentadienyl, palladium(II) ethylcyclopentadienyl, palladium(II) pentamethylcyclopentadienyl, palladium(II) 2,3,7,8,12,13,17,18-octaethyl-21H,23H-porphine, palladium(II) 5,10,15,20-tetraphenyl-21H,23H-porphine, palladium(II) bis(5-[[4-(dimethylamino)phenyl]imino]-8(5H)-quinolinone), palladium(II) 2,11,20,29-tetra-tert-butyl-2,3-naphthalocyanine, palladium(II) 2,9,16,23-tetraphenoxy-29H,31H-phthalocyanine, palladium(II) 5,10,15,20-tetrakis(pentafluorophenyl)-21H,23H-porphine and the 1,4-bis-(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenypimidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)-imidazol-2-ylidene, 1,3-bis(mesitypimidazol-2-ylidene, 1,1'-bis(diphenyl-phosphino)ferrocene, 1,2-bis(diphenylphosphino)ethane, N-methylimidazole, 2,2'-bipyridine, (bicyclo[2.2.1]hepta-2,5-diene), bis(di-tert-butyl (4-dimethyl-aminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

nickel(II) chloride, nickel(II) bromide, nickel(II) iodide, nickel(II) fluoride, nickel(II) hydride, nickel(II) oxide, nickel(II) peroxide, nickel(II) cyanide, nickel(II) sulfate, nickel(II) nitrate, nickel(II) phosphide, nickel(II) boride, nickel(II) chromium oxide, nickel(II) cobalt oxide, nickel(II) carbonate hydroxide, nickel(II) cyclohexane butyrate, nickel(II) hydroxide, nickel(II) molybdate, nickel(II) octanoate, nickel(II) oxalate, nickel(II) perchlorate, nickel(II) phthalocyanine, nickel(II) 5,9,14,18,23,27,32,36-octabutoxy-2,3-naphthalocyanine, nickel(II) sulfamate, nickel(II) perchlorate, nickel(II) thiocyanate, nickel(II) bis(2,2,6,6-tetramethyl-3,5-heptanedionate), nickel(II) propionate, nickel(II) acetate, nickel(II) stearate, nickel(II) 2-ethylhexanoate, nickel(II) acetylacetonate, nickel(II) hexafluoroacetylacetonate, nickel(II) tetrafluoroborate, nickel(II) thiosulfate, nickel(II) trifluoroacetate, nickel(II) phthalocyaninetetrasulfonic acid tetrasodium salt, nickel(II) methyl, nickel(II) cyclopentadienyl, nickel(II) methylcyclopentadienyl, nickel(II) ethylcyclopentadienyl, nickel(II) pentamethylcyclopentadienyl, nickel(II) 2,3,7,8,12,13,17,18-octaethyl-21H,23H-porphine, nickel(II) 5,10,15,20-tetraphenyl-21H,23H-porphine, nickel(II) bis(5-[[4-(dimethylamino)phenyl]imino]-8(5H)-quinolinone), nickel(II) 2,11,20,29-tetra-tert-butyl-2,3-naphthalocyanine, nickel(II) 2,9,16,23-tetraphenoxy-29H,31H-phthalocyanine, nickel(II) 5,10,15,20-tetrakis(pentafluorophenyl)-21H,23H-porphine and the 1,4-bis-(diphenylphosphine)butane, 1,3-bis(diphenylphosphino)propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenypimidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)-imidazol-2-ylidene, 1,3-bis(mesitypimidazol-2-ylidene, 1,1'-bis(diphenyl-phosphino)ferrocene, 1,2-bis(diphenylphosphino)ethane, N-methylimidazole, 2,2'-bipyridine, (bicyclo[2.2.1]hepta-2,5-diene), bis(di-tert-butyl (4-dimethyl-aminophenyl)phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof; platinum(II) chloride, platinum(II) bromide, platinum(II) iodide, platinum(II) fluoride, platinum(II) hydride, platinum(II) oxide, platinum(II) peroxide, platinum(II) cyanide, platinum(II) sulfate, platinum(II) nitrate, platinum(II) phosphide, platinum(II) boride, platinum(II) chromium oxide, platinum(II) cobalt oxide, platinum(II) carbonate hydroxide, platinum(II) cyclohexane butyrate, platinum(II) hydroxide, platinum(II) molybdate, platinum(II) octanoate, platinum(II) oxalate, platinum(II) perchlorate, platinum(II) phthalocyanine, platinum(II) 5,9,14,18,23,27,32,36-octabutoxy-2,3-naphthalocyanine, platinum(II) sulfamate, platinum(II) perchlorate, platinum(II) thiocyanate, platinum(II) bis(2,2,6,6-tetramethyl-3,5-heptanedionate), platinum(II) propionate, platinum(II) acetate, platinum(II) stearate, platinum(II) 2-ethylhexanoate, platinum(II) acetylacetonate, platinum(II) hexafluoroacetylacetonate, platinum(II) tetrafluoroborate, platinum(II) thiosulfate, platinum(II) trifluoroacetate, platinum(II) phthalocyaninetetrasulfonic acid tetrasodium salt, platinum(II) methyl, platinum(II) cyclopentadienyl, platinum(II) methylcyclo-pentadienyl, platinum(II) ethylcyclopentadienyl, platinum(II) pentamethylcyclopentadienyl, platinum(II) 2,3,7,8,12,13,17,18-octaethyl-21H,23H-porphine, platinum(II) 5,10,15,20-tetraphenyl-21H,23H-porphine, platinum(II) bis(5-[[4-(dimethylamino)phenyl]imino]-8(5H)-quinolinone), platinum(II) 2,11,20,29-tetra-tert-butyl-2,3-naphthalocyanine, platinum(11) 2,9,16,23-tetraphenoxy-29H,31H-phthalocyanine, platinum(11) 5,10,15,20-tetrakis-(pentafluorophenyl)-21H,23H-porphine and the 1,4-bis(diphenylphosphine)butane, 1,3-bis(diphenylphosphino)-propane, 2-(2'-di-tert-butylphosphine)biphenyl, acetonitrile, benzonitrile, ethylenediamine, chloroform, 1,2-bis(phenylsulfinyl)ethane, 1,3-bis(2,6-diisopropylphenyl)imidazolidene)(3-chloropyridyl), 2'-(dimethylamino)-2-biphenylyl, dinorbornylphosphine, 2-(dimethylaminomethyl)ferrocene, allyl, bis(diphenylphosphino)butane, (N-succinimidyl)bis-(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)-imidazol-2-ylidene, 1,3-bis(mesitypimidazol-2-ylidene, 1,1'-bis(diphenylphosphino)-ferrocene, 1,2-bis(diphenylphosphino)ethane, N-methylimidazole, 2,2'-bipyridine, (bicyclo[2.2.1]hepta-2,5-diene), bis(di-tert-butyl (4-dimethylaminophenyl)-phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

rhodium chloride, rhodium bromide, rhodium iodide, rhodium fluoride, rhodium hydride, rhodium oxide, rhodium peroxide, rhodium cyanide, rhodium sulfate, rhodium nitrate, rhodium phosphide, rhodium boride, rhodium chromium oxide, rhodium cobalt oxide, rhodium carbonate hydroxide, rhodium cyclohexane butyrate, rhodium hydroxide, rhodium molybdate, rhodium octanoate, rhodium oxalate, rhodium perchlorate, rhodium phthalocyanine, rhodium 5,9,14,18,23,27,32,36-octabutoxy-2,3-naphthalocyanine, rhodium sulfamate, rhodium perchlorate, rhodium thiocyanate, rhodium bis(2,2,6,6-tetramethyl-3,5-heptanedionate), rhodium propionate, rhodium acetate, rhodium stearate, rhodium 2-ethyl hexanoate, rhodium acetylacetonate, rhodium hexafluoroacetylacetonate, rhodium tetrafluoroborate, rhodium thiosulfate, rhodium trifluoroacetate, rhodium phthalocyaninetetrasulfonic acid tetrasodium salt, rhodium methyl, rhodium cyclopentadienyl, rhodium methylcyclopentadienyl, rhodium ethylcyclopentadienyl, rhodium pentamethylcyclopentadienyl, rhodium 2,3,7,8,12,13,17,18-octaethyl-21H,23H-porphine, rhodium 5,10,15,20-tetraphenyl-21H,23H-porphine, rhodium bis(5-[[4-(dimethylamino)phenyl]imino]-8(5H)-quinolinone), rhodium 2,11,20,29-tetra-tert-butyl-2,3-naphthalocyanine, rhodium 2,9,16,23-tetraphenoxy-29H,31H-phthalocyanine, rhodium 5,10,15,20-tetrakis(pentafluorophenyl)-21H,23H-porphine and the 1,4-bis(diphenylphosphine)butane, 1,3-bis(diphenylphosphino)propane, 2-(2'-di-tert-butylphosphine) biphenyl, acetonitrile, benzonitrile, ethylenediamine, chloroform, 1,2-bis(phenylsulfinyl)ethane, 1,3-bis(2,6-diisopropylphenyl)-imidazolidene)(3-chloropyridyl), 2'-(dimethylamino)-2-biphenylyl, dinorbornylphosphine, 2-(dimethylaminomethyl)ferrocene, allyl, bis(diphenylphosphino)-butane, (N-succinimidyl)bis(triphenylphosphine), dimethylphenylphosphine, methyldiphenylphosphine, 1,10-phenanthroline, 1,5-cyclooctadiene, N,N,N',N'-tetramethylethylenediamine, triphenylphosphine, tri-o-tolylphosphine, tricyclohexylphosphine, tributylphosphine, triethylphosphine, 2,2'-bis(diphenylphosphino)-1,1'-binaphthyl, 1,3-bis(2,6-diisopropylphenyl)-imidazol-2-ylidene, 1,3-bis(mesitypimidazol-2-ylidene, 1,1'-bis(diphenylphosphino)-ferrocene, 1,2-bis(diphenylphosphino)ethane, N-methylimidazole, 2,2'-bipyridine, (bicyclo[2.2.1]hepta-2,5-diene), bis(di-tert-butyl(4-dimethylaminophenyl)-phosphine), bis(tert-butyl isocyanide), 2-methoxyethyl ether, ethylene glycol dimethyl ether, 1,2-dimethoxyethane, bis(1,3-diamino-2-propanol), bis(N,N-diethylethylenediamine), 1,2-diaminocyclohexane, pyridine, 2,2':6',2"-terpyridine, diethyl sulfide, ethylene and amine complexes thereof;

potassium hexachloropalladate(IV), sodium hexachloropalladate(IV), ammonium hexachloropalladate(IV), potassium tetrachloropalladate(II), sodium tetrachloropalladate(II), ammonium tetrachloropalladate(II), bromo(tri-tert-butylphosphine)palladium(I) dimer, (2-methylallyl)palladium(II) chloride dimer, bis(dibenzylideneacetone)palladium(O), tris(dibenzylideneacetone)dipalladium(O), tetrakis(triphenylphosphine)palladium(O), tetrakis(tricyclohexylphosphine)-palladium(O), bis[1,2-bis(diphenylphosphine)ethane]palladium(O), bis(3,5,3',5'-dimethoxydibenzylideneacetone)palladium(O), bis(tri-tert-butylphosphine)-palladium(O), meso-tetraphenyltetrabenzoporphinepalladium, tetrakis-(methyldiphenylphosphine)palladium (O), tris(3,3',3"-phophinidyne-tris(benzenesulfonato)palladium(O) nonasodium salt, 1,3-bis(2,4,6-trimethyl-phenypimidazol-2-ylidene(1,4-naphthoquinone)palladium(O), 1,3-bis(2,6-diisopropylphenypimidazol-2-ylidene(1,4-naphthoquinone)palladium(O) and the chloroform complex thereof;

allylnickel(II) chloride dimer, ammonionickel(II) sulfate, bis(1,5-cyclooca-diene)nickel(O), bis(triphenylphosphine) dicarbonylnickel(O), tetrakis(triphenyl-phosphine)nickel (O), tetrakis(triphenyl phosphite)nickel(O), potassium hexafluoronickelate(IV), potassium tetracyanonickelate(II), potassium nickel(IV) paraperiodate, dilithium tetrabromonickelate(II), potassium tetracyanonickelate(II); platinum(IV) chloride, platinum(IV) oxide, platinum(IV) sulfide, potassium hexachloroplatinate(IV), sodium hexachloroplatinate (IV), ammonium hexachloroplatinate(IV), potassium tetrachloroplatinate(II), ammonium tetrachloroplatinate(II), potassium tetracyanoplatinate(II), trimethyl(methylcyclopentadienyl)platinum(IV), cis-diamminetetrachloroplatinum(IV), potassium trichloro(ethylene)platinate(II), sodium hexahydroxyplatinate(IV), tetraamineplatinum(II) tetrachloroplatinate(II), tetrabutylammonium hexachloroplatinate (IV), ethylenebis(triphenylphosphine)platinum(O), platinum(O) 1,3-divinyl-1,1,3,3-tetramethyldisiloxane, platinum (O) 2,4,6,8-tetramethyl-2,4,6,8-tetravinylcyclotetrasiloxane, tetrakis(triphenylphosphine)platinum(O), platinum octaethylporphyrin, chloroplatinic acid, carboplatin; chlorobis(ethylene)rhodium dimer, hexarhodium hexadecacarbonyl, chloro-(1,5-cyclooctadiene)rhodium dimer, chloro(norbornadiene)rhodium dimer, chloro(1,5-hexadiene)rhodium dimer.

The ligands preferably comprise phosphines of the formula (VI)

$$PR^8_3 \qquad (VI)$$

in which the $R^8$ radicals are each independently hydrogen, straight-chain, branched or cyclic $C_1$-$C_{20}$-alkyl, $C_6$-$C_{20}$-alkylaryl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or derivatives thereof and/or phenyl substituted by at least one $R^9$, or naphthyl substituted by at least one $R^9$. Each $R^9$ is independently hydrogen, fluorine, chlorine, bromine, iodine, $NH_2$, nitro, hydroxyl, cyano, formyl, straight-chain, branched or cyclic $C_1$-$C_{20}$-alkyl, $C_1$-$C_{20}$-alkoxy, $HN(C_1$-$C_{20}$-alkyl), $N(C_1$-$C_{20}$-alkyl)$_2$, —$CO_2$—($C_1$-$C_{20}$-alkyl), —$CON(C_1$-$C_{20}$-alkyl)$_2$, —OCO($C_1$-$C_{20}$-alkyl), NHCO($C_1$-$C_{20}$-alkyl), $C_1$-$C_{20}$-acyl, —$SO_3M$, —$SO_2N(R^{10})M$, —$CO_2M$, —$PO_3M_2$, —$AsO_3M_2$, —$SiO_2M$, —$C(CF_3)_2OM$ (M=H, Li, Na or K), where $R^{10}$ is hydrogen, fluorine, chlorine, bromine, iodine, straight-chain, branched or cyclic $C_1$-$C_{20}$-alkyl, $C_2$-$C_{20}$-alkenyl, $C_2$-$C_{20}$-alkynyl, $C_1$-$C_{20}$-carboxylate, $C_1$-$C_{20}$-alkoxy, $C_2$-$C_{20}$-alkenyloxy, $C_2$-$C_{20}$-alkynyloxy, $C_2$-$C_{20}$-alkoxycarbonyl, $C_1$-$C_{20}$-alkylthio, $C_1$-$C_{20}$-alkylsulfonyl, $C_1$-$C_{20}$-alkylsulfinyl, silyl and/or their derivatives, aryl, $C_6$-$C_{20}$-arylalkyl, $C_6$-$C_{20}$-alkylaryl, phenyl and/or biphenyl. Preferably, the $R^8$ groups are all identical.

Suitable phosphines (VI) are for example trimethylphosphine, triethylphosphine, tripropylphosphine, triisopropylphosphine, tributylphosphine, triisobutylphosphine, triisopentylphosphine, trihexylphosphine, tricyclohexylphosphine, trioctyl-phosphine, tridecylphosphine, triphenylphosphine, diphenylmethylphosphine, phenyldimethylphosphine, tri(o-tolyl)phosphine, tri(p-tolyl)phosphine, ethyldiphenylphosphine, dicyclohexylphenylphosphine, 2-pyridyldiphenyl-phosphine, bis(6-methyl-2-pyridyl)phenylphosphine, tri(p-chlorophenyl)phosphine, tri(p-methoxyphenyl)phosphine, diphenyl(2-sulfonatophenyl)phosphine; potassium, sodium and ammonium salts of diphenyl(3- sulfonatophenyl)phosphine, bis(4,6-dimethyl-3-sulfonatophenyl)(2,4-dimethylphenyl)phosphine, bis(3-sulfonatophenyl)phenyl-phosphines, tris(4,6-dimethyl-3-sulfonatophenyl)-phosphines, tris(2-sulfonatophenyl) phosphines, tris(3-sulfonatophenyl)phosphines; 2-bis(diphenylphosphinoethyl)trimethylammonium iodide, 2'-dicyclohexylphosphino-2,6-dimethoxy-3-sulfonato-1,1'-biphenyl sodium salt, trimethyl phosphite and/or triphenyl phosphite.

The ligands more preferably comprise bidentate ligands of the formula (VII)

In this formula, each M" is independently N, P, As or Sb.

The two M" are preferably the same, and M" is more preferably a phosphorus atom.

Each $R^8$ group independently represents the radicals described under formula (VI). The $R^8$ groups are preferably all identical.

Z is preferably a bivalent bridging group which contains at least 1 bridging atom, preferably from 2 to 6 bridging atoms.

Bridging atoms can be selected from carbon, nitrogen, oxygen, silicon and sulfur atoms. Z is preferably an organic bridging group containing at least one carbon atom. Z is preferably an organic bridging group containing 1 to 6 bridging atoms, of which at least two are carbon atoms, which may be substituted or unsubstituted.

Preferred Z groups are —$CH_2$—, —$CH_2$—$CH_2$—, —$CH_2$—$CH_2$—$CH_2$—, —$CH_2$—$CH(CH_3)$—$CH_2$—, —$CH_2$—$C(CH_3)_2$—$CH_2$—, —$CH_2$—$C(C_2H_5)$—$CH_2$—, —$CH_2$—$Si(CH_3)_2$—$CH_2$—, —$CH_2$—O—$CH_2$—, —$CH_2$—$CH_2$—$CH_2$—$CH_2$—, —$CH_2$—$CH(C_2H_5)$—$CH_2$—, —$CH_2$—CH(n-Pr)—CH and —$CH_2$—CH(n-Bu)—$CH_2$—, substituted or unsubstituted 1,2-phenyl, 1,2-cyclohexyl, 1,1'- or 1,2-ferrocenyl radicals, 2,2"-(1,1"-biphenyl), 4,5-xanthene and/or oxydi-2,1-phenylene radicals.

Examples of suitable bidentate phosphine ligands (VII) are 1,2-bis-(dimethylphosphino)-ethane, 1,2-bis(diethylphosphino)ethane, 1,2-bis-(dipropylphosphino)ethane, 1,2-bis(diisopropylphosphino)ethane, 1,2-bis(dibutylphosphino)ethane, 1,2-bis(di-tert-butylphosphino)ethane, 1,2-bis-(dicyclohexylphosphino)ethane, 1,2-bis(diphenylphosphino)ethane; 1,3-bis(dicyclohexylphosphino)propane, 1,3-bis(diisopropyl-phosphino)propane, 1,3-bis(di-tert-butylphosphino)propane, 1,3-bis(diphenyl-phosphino)propane; 1,4-bis(diisopropylphosphino)butane, 1,4-bis(diphenylphosphino)butane; 1,5-bis(dicyclohexylphosphino) pentane; 1,2-bis(di-tert-butylphosphino)benzene, 1,2-bis(diphenylphosphino)benzene, 1,2-bis(dicyclohexylphosphino)benzene, 1,2-bis(dicyclopentylphosphino)benzene, 1,3-bis(di-tert-butylphosphino)benzene, 1,3-bis(diphenylphosphino)benzene, 1,3-bis(dicyclohexylphosphino) benzene, 1,3-bis(dicyclopentylphosphino)benzene; 9,9-dimethyl-4,5-bis(diphenylphosphino)-xanthene, 9,9-dimethyl-4,5-bis(diphenylphosphino)-2,7-di-tert-butylxanthene, 9,9-dimethyl-4,5-bis(di-tert-butylphosphino)xanthene, 1,1'-bis(diphenylphosphino)-ferrocene, 2,2'-bis(diphenylphosphino)-1,1'-binaphthyl, 2,2'-bis(di-p-tolylphosphino)-1,1'-binaphthyl, (oxydi-2,1-phenylene)bis(diphenylphosphine), 2,5-(diisopropylpholano)benzene, 2,3-O-isopropylidene-2,3-dihydroxy-1,4-bis(diphenylphosphino)butane, 2,2'-bis(di-tert-butylphosphino)-1,1'-biphenyl, 2,2'-bis(dicyclohexylphosphino)-1,1'-biphenyl, 2,2'-bis(diphenylphosphino)-1,1'-biphenyl, 2-(di-tert-butylphosphino)-2'-(N,N-dimethylamino)biphenyl, 2-(dicyclohexylphosphino)-2'-(N,N-dimethylamino)biphenyl, 2-(diphenylphos-phino)-2'-(N, N-dimethylamino)biphenyl, 2-(diphenylphosphino)ethylamine, 2-[2-(diphenylphosphino)ethyl] pyridine; potassium, sodium and ammonium salts of 1,2-bis (di-4-sulfonatophenylphosphino)benzene, (2,2'-bis[[bis(3-sulfonatophenyl)-phosphino]methyl]-4,4',7,7'-tetrasulfonato-1,1'-binaphthyl, (2,2'-bis[[bis(3-sulfonato-phenyl) phosphino]methyl]-5,5'-tetrasulfonato-1,1'-biphenyl, (2,2'-bis[[bis(3-sulfonato-phenyl)phosphino]methyl]-1,1'-binaphthyl, (2,2'-bis[[bis(3-sulfonatophenyl)phosphino]-methyl]-1,1'-biphenyl, 9,9-dimethyl-4,5-bis(diphenylphosphino)-2,7-sulfonatoxanthene, 9,9-dimethyl-4,5-bis(di-tert-butylphosphino)-2,7-sulfonatoxanthene, 1,2-bis(di-4-sulfonatophenylphosphino)-benzene, meso-tetrakis(4-sulfonatophenyl)porphine, meso-tetrakis(2,6-dichloro-3-sulfonatophenyl)porphine, meso-tetrakis(3-sulfonatomesityl)porphine, tetrakis(4-carboxyphenyl)porphine and 5,11,17,23-sulfonato-25,26,27,28-tetrahydroxycalix[4] arene.

Moreover, the ligands of the formula (VI) and (VII) can be attached to a suitable polymer or inorganic substrate by the $R^8$ radicals and/or the bridging group.

The molar transition metal/ligand ratio of the catalyst system is in the range from 1:0.01 to 1:100, preferably in the range from 1:0.05 to 1:10 and more preferably in the range from 1:1 to 1:4.

The reactions in the process stages a), b) and c) preferably take place, if desired, in an atmosphere comprising further gaseous constituents such as nitrogen, oxygen, argon, carbon dioxide for example; the temperature is in the range from −20 to 340° C., more particularly in the range from 20 to 180° C., and total pressure is in the range from 1 to 100 bar.

The products and/or the transition metal and/or the transition metal compound and/or catalyst system and/or the ligand and/or the starting materials are optionally isolated after the process stages a), b) and c) by distillation or rectification, by crystallization or precipitation, by filtration or centrifugation, by adsorption or chromatography or other known methods.

According to the present invention, solvents, auxiliaries and any other volatile constituents are removed by distillation, filtration and/or extraction for example.

The reactions in the process stages a), b) and c) are preferably carried out, if desired, in absorption columns, spray towers, bubble columns, stirred tanks, trickle bed reactors, flow tubes, loop reactors and/or kneaders.

Suitable mixing elements include for example anchor, blade, MIG, propeller, impeller and turbine stirrers, cross beaters, disperser disks, hollow (sparging) stirrers, rotor-stator mixers, static mixers, Venturi nozzles and/or mammoth pumps.

The intensity of mixing experienced by the reaction solutions/mixtures preferably corresponds to a rotation Reynolds number in the range from 1 to 1 000 000 and preferably in the range from 100 to 100 000.

Preferably, the respective reactants etc. are mixed intensively with an energy input in the range from 0.080 to 10 kW/m³, preferably 0.30-1.65 kW/m³.

During the reaction, the catalyst A is preferably homogeneous and/or heterogeneous in action.

Preferably, the catalyst A is generated in situ before the reaction and/or at the start of the reaction and/or during the reaction.

Preferably, the particular heterogeneous catalyst acts during the reaction as a suspension or bound to a solid phase.

The reactions of the present invention can be carried out in liquid phase, in the gas phase or else in supercritical phase. The catalyst A is preferably used in the case of liquids in homogeneous form or as a suspension, while a fixed bed arrangement is advantageous in the case of gas phase or supercritical operation.

Suitable solvents are water, alcohols, e.g. methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc. Preference is further given to glycols, e.g. ethylene glycol, 1,2-propanediol, 1,3-propanediol, 1,3-butanediol, 1,4-butanediol, diethylene glycol etc.; aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloro-ethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone etc.; esters, such as methyl formate, methyl acetate, ethyl acetate, n-propyl acetate, and n-butyl acetate, etc.; carboxylic acids, such as formic acid, acetic acid, propionic acid, butyric acid, etc., each alone or in combination with one another.

Suitable solvents also encompass the phosphinic acid sources and olefins used. These have advantages in the form of higher space-time yield.

Preferably, the reaction is carried out under the autogenous vapor pressure of the olefin and/or of the solvent.

Preferably, $R^1$, $R^2$, $R^3$ and $R^4$ of olefin (IV) are the same or different and are each independently H, methyl, ethyl, n-propyl, isopropyl, n-butyl, isobutyl, tert-butyl and/or phenyl.

Preference is also given to using functionalized olefins such as allyl isothio-cyanate, allyl methacrylate, 2-allylphenol, N-allylthiourea, 2-(allylthio)-2-thiazoline, allyltrimethylsilane, allyl acetate, allyl acetoacetate, allyl alcohol, allylamine, allylbenzene, allyl cyanide, allyl cyanoacetate, allylanisole, trans-2-pentenal, cis-2-pentenenitrile, 1-penten-3-ol, 4-penten-1-ol, 4-penten-2-ol, trans-2-hexenal, trans-2-hexen-1-ol, cis-3-hexen-1-ol, 5-hexen-1-ol, styrene, -methylstyrene, 4-methylstyrene, vinyl acetate, 9-vinylanthracene, 2-vinylpyridine, 4-vinylpyridine and/or 1-vinyl-2-pyrrolidone.

Preferably, the reaction is effected at a pressure of the olefin of 0.01-100 bar, more preferably at a pressure of the olefin of 0.1-10 bar.

Preferably, the reaction is effected in a molar phosphinic acid/olefin ratio of from 1:10 000 to 1:0.001, more preferably of 1:30 to 1:0.01.

Preferably, the reaction is effected in a molar phosphinic acid/catalyst ratio of from 1:1 to 1:0.00000001, more preferably at 1:0.01 to 1:0.000001.

Preferably, the reaction is effected in a molar phosphinic acid/solvent ratio of from 1:10 000 to 1:0, more preferably at 1:50 to 1:1.

One process of the invention for preparing compounds of the formula (II) comprises reacting a phosphinic acid source with olefins in the presence of a catalyst and freeing the product (II) (alkylphosphonous acid, salts or esters) of catalyst, transition metal, transition metal compound, ligand, complexing agent, salts and by-products.

The present invention provides that the catalyst, the catalyst system, the transition metal and/or the transition metal compound are separated off by adding an auxiliary 1 and removing the catalyst, the catalyst system, the transition metal and/or the transition metal compound by extraction and/or filtration.

The present invention provides that the ligand and/or complexing agent is separated off by extraction with auxiliary 2 and/or distillation with auxiliary 2.

Auxiliary 1 is preferably water and/or at least one member of the group of metal scavengers. Preferred metal scavengers are metal oxides, such as aluminum oxide, silicon dioxide, titanium dioxide, zirconium dioxide, zinc oxide, nickel oxide, vanadium oxide, chromium oxide, magnesium oxide, Celite®, kieselguhr; metal carbonates, such as barium carbonate, calcium carbonate, strontium carbonate; metal sulfates, such as barium sulfate, calcium sulfate, strontium sulfate; metal phosphates, such as aluminum phosphate, vanadium phosphate, metal carbides, such as silicone carbide; metal aluminates, such as calcium aluminate; metal silicates, such as aluminum silicate, chalks, zeolites, bentonite, montmorillonite, hectorite; functionalized silicates, functionalized silica gels, such as SiliaBond®, QuadraSil™; functionalized polysiloxanes, such as Deloxan®; metal nitrides, carbon, activated carbon, mullite, bauxite, antimonite, scheelite, perovskite, hydrotalcite, functionalized and unfunctionalized cellulose, chitosan, keratin, heteropolyanions, ion exchangers, such as Amberlite™, Amberjet™, Ambersep™, Dowex®, Lewatit®, ScavNet®; functionalized polymers, such as Chelex®, QuadraPure™, Smopex®, PolyOrgs®; polymer-bound phosphanes, phosphane oxides, phosphinates, phosphonates, phosphates, amines, ammonium salts, amides, thioamides, ureas, thioureas, triazines, imidazoles, pyrazoles, pyridines, pyrimidines, pyrazines, thiols, thiol ethers, thiol esters, alcohols, alkoxides, ethers, esters, carboxylic acids, acetates, acetals, peptides, hetarenes, polyethyleneimine/silicon dioxide, and/or dendrimers.

Preferably, auxiliary 1 is added in amounts corresponding to 0.1-40% by weight loading of the metal on auxiliary 1.

Preferably, auxiliary 1 is used at temperatures of 20-90° C.

Preferably, the residence time of auxiliary 1 is 0.5-360 minutes.

Auxiliary 2 is preferably the aforementioned solvent of the present invention, as preferably used in process stage a).

The esterification of the ethylenedialkylphosphinic acid (III) or of the alkylphosphonous acid derivatives (II), and of the phosphinic acid source (I) to form the corresponding esters can be achieved, for example, by reaction with higher-boiling alcohols by removing the resultant water by azeotropic distillation, or by reaction with epoxides (alkylene oxides).

Preferably, following step a), the alkylphosphonous acid (II) is directly esterified with an alcohol of the formula M-OH and/or M'—OH or by reaction with alkylene oxides, as indicated below.

Preferred alcohols M-OH are primary, secondary or tertiary alcohols having a carbon chain length of $C_1$-$C_{18}$.

Particular preference is given to methanol, ethanol, propanol, isopropanol, n-butanol, 2-butanol, tert-butanol, amyl alcohol and/or hexanol.

Preferred alcohols M'—OH are ethylene glycol, 1,2-propylene glycol, 1,3-propylene glycol, 1,4-butanediol, 2,2-dimethylpropane-1,3-diol, neopentyl glycol, 1,6-hexanediol, 1,4-cyclohexanedimethanol, glycerol, trishydroxymethylethane, trishydroxymethylpropane, pentaerythritol, sorbitol, mannitol, α-naphthol, polyethylene glycols, polypropylene glycols and/or EO-PO block polymers.

Suitable alcohols M-OH and M'—OH are mono- or polyhydric unsaturated alcohols having a carbon chain length of $C_1$-$C_{18}$, for example n-but-2-en-1-ol, 1,4-butenediol and allyl alcohol.

Suitable alcohols M-OH and M'—OH are also reaction products of monohydric alcohols with one or more molecules of alkylene oxides, preferably with ethylene oxide and/or 1,2-propylene oxide. Preference is given to 2-methoxyethanol, 2-ethoxyethanol, 2-n-butoxyethanol, 2-(2'-ethyl hexyloxy)ethanol, 2-n-dodecoxy-ethanol, methyl diglycol, ethyl diglycol, isopropyl diglycol, fatty alcohol polyglycol ethers and aryl polyglycol ethers.

Preferred alcohols M-OH and M'—OH are also reaction products of polyhydric alcohols with one or more molecules of alkylene oxide, more particularly diglycol and triglycol and also adducts of 1 to 6 molecules of ethylene oxide or propylene oxide onto glycerol, trishydroxymethylpropane or pentaerythritol.

Alcohols M-OH and M'—OH used may also be reaction products of water with one or more molecules of alkylene oxide. Preference is given to polyethylene glycols and poly-1,2-propylene glycols of various molecular sizes having an average molecular weight of 100-1000 g/mol and more preferably of 150-350 g/mol.

Preferred alcohols M-OH and M'—OH are also reaction products of ethylene oxide with poly-1,2-propylene glycols or fatty alcohol propylene glycols; similarly reaction products of 1,2-propylene oxide with polyethylene glycols or fatty alcohol ethoxylates. Preference is given to such reaction products with an average molecular weight of 100-1000 g/mol, more preferably of 150-450 g/mol.

Usable alcohols M-OH and M'—OH are also reaction products of alkylene oxides with ammonia, primary or secondary amines, hydrogen sulfide, mercaptans, oxygen acids of phosphorus and $C_2$-$C_6$ dicarboxylic acids. Suitable reaction products of ethylene oxide with nitrogen compounds are triethanolamine, methyldiethanolamine, n-butyldiethanol-amine, n-dodecyldiethanolamine, dimethylethanolamine, n-butylmethylethanolamine, di-n-butylethanolamine, n-dodecylmethylethanolamine, tetrahydroxyethylethylenediamine or pentahydroxyethyldiethylenetriamine.

Preferred alkylene oxides are ethylene oxide, 1,2-propylene oxide, 1,2-epoxy-butane, 1,2-epoxyethylbenzene, (2,3-epoxypropyl)benzene, 2,3-epoxy-1-propanol and 3,4-epoxy-1-butene.

Suitable solvents are the solvents mentioned in process step a) and also the alcohols and alkylene oxides used. These offer advantages in the form of a higher space-time yield.

The reaction is preferably carried out under the autogenous vapor pressure of the alcohol and/or alkylene oxide used and/or of the solvent.

Preferably, the reaction is carried out at a pressure of the alcohol and/or alkylene oxide used of 0.01-100 bar, more preferably at a pressure of the alcohol of 0.1-10 bar.

Preferably, the reaction is carried out at a temperature of from −20 to 340° C., more preferably at a temperature of from 20 to 180° C.

Preferably, the reaction is carried out at a total pressure of from 1 to 100 bar.

Preferably, the reaction is carried out in a molar ratio of the alcohol or alkylene oxide component to the phosphinic acid source (I) or alkylphosphonous acid (II) or ethylenedialkylphosphinic acid (III) of from 10 000:1 to 0.001:1, more preferably in a ratio of 1000:1 to 0.01:1.

Preferably, the reaction is carried out in a molar ratio of the phosphinic acid source (I) or alkylphosphonous acid (II) or ethylenedialkylphosphinic acid (III) to the solvent of from 1:10 000 to 1:0, more preferably in a molar phosphinic acid/solvent ratio of from 1:50 to 1:1.

Suitable solvents are those mentioned for step a).

Preferably, the alkylphosphonous acids (II) are reacted with the acetylenic compound (V) at a temperature of 0 to 250° C., more preferably at a temperature of 20 to 150° C. and especially at a temperature of 40 to 100° C.

Preferably, the atmosphere in the reaction with the acetylenic compound (V) consists to an extent of 50 to 99.9% by weight of constituents of the solvent and of the acetylenic compound (V), preferably 70 to 95%.

Preferably, the reaction during the addition of the acetylenic compound (V) is effected at a pressure of 1 to 20 bar.

The subject matter of the present invention especially also comprises a process in which an alkylphosphonous acid (II) is reacted with an acetylenic compound (V) in the presence of UV radiation, and the former is removed continuously from the reaction mixture by circulation filtration and the spent alkylphosphonous acid (II) is likewise continuously replaced by new material.

In a further embodiment of the process, the product mixture obtained after process stage a) and/or b) is worked up.

In a further embodiment of the process, the product mixture obtained after process stage a) is worked up, and then the ethylenedialkylphosphinic acids and/or esters and alkali metal salts thereof which are obtained after process stage b) are converted in process stage c).

The ethylenedialkylphosphinic acid (III), or salt thereof, can subsequently be converted to further metal salts.

Preferably, the metal compounds used in process stage c) are compounds of the metals Mg, Ca, Al, Sb, Sn, Ge, Ti, Fe, Zr, Zn, Ce, Bi, Sr, Mn, Li, Na, K, more preferably those of Mg, Ca, Al, Ti, Zn, Sn, Ce, Fe.

Suitable solvents for process stage c) are those as used further up in process stage a).

Preferably, the reaction in process stage c) is effected in an aqueous medium.

Preferably, in process stage c), the ethylenedialkylphosphinic acids (III), esters and/or alkali metal salts thereof, obtained after process stage b) are reacted with metal compounds of Mg, Ca, Al, Zn, Ti, Sn, Zr, Ce or Fe to give the ethylenedialkylphosphinic salts (III) of these metals.

This reaction is effected in a molar ratio of ethylenedialkylphosphinic acid/ester/salt (III) to metal of 8:1 to 1:8 (for tetravalent metal ions or metals with a stable tetravalent oxidation state), of 6:1 to 1:6 (for trivalent metal ions or metals with a stable trivalent oxidation state), of 4:1 to 1:4 (for divalent metal ions or metals with a stable divalent oxidation state) and of 3:1 to 1:6 (for monovalent metal ions or metals with a stable monovalent oxidation state).

Preferably, ethylenedialkylphosphinic ester/salt (III) obtained in process stage b) is converted to the corresponding ethylenedialkylphosphinic acid, and the latter is reacted in process stage c) with metal compounds of Mg, Ca, Al, Zn, Ti, Sn, Zr, Ce or Fe to give the ethylenedialkylphosphinic salts (III) of these metals.

Preferably, ethylenedialkylphosphinic acid/ester (III) obtained in process stage b) is converted to an ethylenedialkylphosphinic acid alkali metal salt, and the latter is reacted in process stage c) with metal compounds of Mg, Ca, Al, Zn, Ti, Sn, Zr, Ce or Fe to give the ethylenedialkylphosphinic salts (III) of these metals.

The metal compounds of Mg, Ca, Al, Zn, Ti, Sn, Zr, Ce or Fe for process stage c) preferably comprise metals, metal oxides, hydroxides, oxide hydroxides, borates, carbonates, hydroxocarbonates, hydroxocarbonate hydrates, mixed metal hydroxocarbonates, mixed metal hydroxocarbonate hydrates, phosphates, sulfates, sulfate hydrates, hydroxosulfate hydrates, mixed metal hydroxosulfate hydrates, oxysulfates, acetates, nitrates, fluorides, fluoride hydrates, chlorides, chloride hydrates, oxychlorides, bromides, iodides, iodide hydrates, carboxylic acid derivatives and/or alkoxides.

The metal compounds preferably comprise aluminum chloride, aluminum hydroxide, aluminum nitrate, aluminum sulfate, titanyl sulfate, zinc nitrate, zinc oxide, zinc hydroxide and/or zinc sulfate.

Also suitable are aluminum metal, fluoride, hydroxychloride, bromide, iodide, sulfide, selenide; phosphide, hypophosphite, antimonide, nitride; carbide, hexafluorosilicate; hydride, calcium hydride, borohydride; chlorate; sodium aluminum sulfate, aluminum potassium sulfate, aluminum ammonium sulfate, nitrate, metaphosphate, phosphate, silicate, magnesium silicate, carbonate, hydrotalcite, sodium carbonate, borate; thiocyanate; oxide, oxide hydroxide, their corresponding hydrates and/or polyaluminum hydroxy compounds, which preferably have an aluminum content of 9% to 40% by weight.

Also suitable are aluminum salts of mono-, di-, oligo-, polycarboxylic acids, for example, aluminum diacetate, acetotartrate, formate, lactate, oxalate, tartrate, oleate, palmitate, stearate, trifluoromethanesulfonate, benzoate, salicylate, 8-oxyquinolate.

Likewise suitable are elemental, metallic zinc and also zinc salts, for example zinc halides (zinc fluoride, zinc chlorides, zinc bromide, zinc iodide).

Also suitable are zinc borate, carbonate, hydroxide carbonate, silicate, hexafluorosilicate, stannate, hydroxide stannate, magnesium aluminum hydroxide carbonate; nitrate, nitrite, phosphate, pyrophosphate; sulfate, phosphide, selenide, telluride and zinc salts of the oxo acids of the seventh main group (hypohalites, halites, halates, for example zinc iodate, perhalates, for example zinc perchlorate); zinc salts of the pseudohalides (zinc thiocyanate, zinc cyanate, zinc cyanide); zinc oxides, peroxides, hydroxides or mixed zinc oxide hydroxides.

Preference is given to zinc salts of the oxo acids of transition metals (for example zinc chromate(VI) hydroxide, chromite, permanganate, molybdate).

Also suitable are zinc salts of mono-, di-, oligo-, polycarboxylic acids, for example zinc formate, acetate, trifluoroacetate, propionate, butyrate, valerate, caprylate, oleate, stearate, oxalate, tartrate, citrate, benzoate, salicylate, lactate, acrylate, maleate, succinate, salts of amino acids (glycine), of acidic hydroxyl functions (zinc phenoxide etc), zinc p-phenolsulfonate, acetylacetonate, stannate, dimethyldithiocarbamate, trifluoromethanesulfonate.

In the case of titanium compounds, preference is given to metallic titanium and, as is the case for titanium(III) and/or (IV), to the chloride, nitrate, sulfate, formate, acetate, bromide, fluoride, oxychloride, oxysulfate, oxide, n-propoxide, n-butoxide, isopropoxide, ethoxide, 2-ethylhexyl oxide.

Also suitable is metallic tin and also tin salts (tin(II) and/or (IV) chloride); tin oxides and tin alkoxide such as, for example, tin(IV) tert-butoxide.

Cerium(III) fluoride, chloride and nitrate are also suitable.

In the case of zirconium compounds, metallic zirconium is preferred, as are zirconium salts such as zirconium chloride, zirconium sulfate, zirconyl acetate, zirconyl chloride. Zirconium oxides and also zirconium(IV) tert-butoxide are also preferred.

The reaction in process stage c) is effected at a solids content of the ethylenedialkylphosphinic salts of from 0.1 to 70% by weight, preferably 5 to 40% by weight.

The reaction in process stage c) is effected at a temperature of 20 to 250° C., preferably at a temperature of 80 to 120° C.

The reaction in process stage c) is effected at a pressure between 0.01 and 1000 bar, preferably at 0.1 to 100 bar.

The reaction in process stage c) is preferably effected over a reaction time of $1*10^{-7}$ to 1000 h.

Preferably, the ethylenedialkylphosphinic salt (III) removed after process stage c) from the reaction mixture by filtration and/or centrifugation is dried.

Preferably, the product mixture obtained after process stage b) is reacted with the metal compounds without further purification.

Preferred solvents are the solvents mentioned in process step a).

The reaction in process stage b) and/or c) is preferably effected in the solvent system given by stage a).

The reaction in process stage c) is preferably in a modified given solvent system. Acidic components, solubilizers, foam inhibitors, etc are added for this purpose.

In a further embodiment of the process, the product mixture obtained after process stage a), b) and/or c) is worked up.

In a further embodiment of the process, the product mixture obtained after process stage b) is worked up and thereafter the ethylenedialkylphosphinic acids (III), and/or salts or esters thereof, obtained after process stage b) are reacted in process stage c) with the metal compounds.

Preferably, the product mixture after process stage b) is worked up by isolating the ethylenedialkylphosphinic acids (III), and/or salts or esters thereof, by removing the solvent system, for example by evaporative concentration.

Preferably, the ethylenedialkylphosphinic salt (III) of the metals Mg, Ca, Al, Zn, Ti, Sn, Zr, Ce or Fe selectively has a residual moisture content of 0.01% to 10% by weight, preferably of 0.1% to 1% by weight, an average particle size of 0.1 to 2000 µm, preferably of 10 to 500 µm, a bulk density of 80 to 800 g/L, preferably of 200 to 700 g/L, and a Pfrengle flowability of 0.5 to 10, preferably of 1 to 5.

The moldings, films, filaments and fibers more preferably contain 5% to 30% by weight of the ethylenedialkylphosphinic acid/ester/salts produced as described herein, 40% to 85% by weight of polymer or mixtures thereof, 5% to 40% by weight of additives and 5% to 40% by weight of filler, where the sum of the components is always 100% by weight.

The additives preferably comprise antioxidants, antistats, blowing agents, further flame retardants, heat stabilizers, impact modifiers, processing aids, lubricants, light stabilizers, antidripping agents, compatibilizers, reinforcing agents, fillers, nucleus-forming agents, nucleating agents, additives for laser marking, hydrolysis stabilizers, chain extenders, color pigments, softeners, plasticizers and/or plasticizing agents.

Preference is given to a flame retardant containing 50% to 99% by weight of the ethylenedialkylphosphinic acid (III), esters and salts, and 0.1% to 50% by weight of further additives, more preferably diols.

Preferred additives are also aluminum trihydrate, antimony oxide, brominated aromatic or cycloaliphatic hydrocarbons, phenols, ethers, chloroparaffin, hexachlorocyclopenta-diene adducts, red phosphorus, melamine derivatives, melamine cyanurates, ammonium polyphosphates and magnesium hydroxide. Preferred additives are also further flame retardants, more particularly salts of dialkylphosphinic acids.

More particularly, the present invention relates to the use of the inventive ethylenedialkylphosphinic acid (III), esters and salts as flame retardants or as an intermediate in the manufacture of flame retardants for thermoplastic polymers such as polyesters, polystyrene or polyamide and for thermoset polymers such as unsaturated polyester resins, epoxy resins, polyurethanes or acrylates.

Suitable polyesters derive from dicarboxylic acids and their esters and diols and/or from hydroxycarboxylic acids or the corresponding lactones. It is particularly preferable to use terephthalic acid and ethylene glycol, 1,3-propanediol and 1,3-butanediol.

Suitable polyesters include polyethylene terephthalate, polybutylene terephthalate (Celanex® 2500, Celanex® 2002, from Celanese; Ultradur®, from BASF), poly-1,4-dimethylolcyclohexane terephthalate, polyhydroxybenzoates, and also block polyether esters derived from polyethers having hydroxyl end groups; and also polyesters modified with polycarbonates or MBS.

Synthetic linear polyesters having permanent flame retardancy are composed of dicarboxylic acid components, diol components of the present invention ethylenedialkylphosphinic acids and esters, or of the ethylenedialkylphosphinic acids and esters produced by the process of the present invention as phosphorus-containing chain members. The phosphorus-containing chain members account for 2%-20% by weight of the dicarboxylic acid component of the polyester. The resulting phosphorus content in the polyester is preferably 0.1%-5% by weight, more preferably 0.5%-3% by weight.

The steps which follow can be carried out with or by addition of the compounds produced in accordance with the present invention.

Preferably, the molding composition is produced from the free dicarboxylic acid and diols by initially esterifying directly and then polycondensing.

When proceeding from dicarboxylic esters, more particularly dimethyl esters, it is preferable to first transesterify, and then to polycondense by using catalysts customary for this purpose.

Polyester production may preferably proceed by adding customary additives (crosslinking agents, matting agents and stabilizing agents, nucleating agents, dyes and fillers, etc.) in addition to the customary catalysts.

The esterification and/or transesterification involved in polyester production is preferably carried out at temperatures of 100-300° C., more preferably at 150-250° C.

The polycondensation in the polyester production preferably takes place at pressures between 0.1 to 1.5 mbar and temperatures of 150-450° C., more preferably at 200-300° C.

The flame-retardant polyester molding compositions produced in accordance with the present invention are preferably used in polyester moldings.

Preferred polyester moldings are filaments, fibers, films and moldings containing mainly terephthalic acid as dicarboxylic acid component and mainly ethylene glycol as diol component.

The resulting phosphorus content in filaments and fibers produced from flame-retardant polyesters is preferably 0.1%-18%, more preferably 0.5%-15% by weight, and in the case of films 0.2%-15%, preferably 0.9%-12% by weight.

Suitable polystyrenes are polystyrene, poly(p-methylstyrene) and/or poly(alpha-methylstyrene).

Suitable polystyrenes preferably comprise copolymers of styrene or alpha-methylstyrene with dienes or acrylic derivatives, for example styrene-butadiene, styrene-acrylonitrile, styrene-alkyl methacrylate, styrene-butadiene-alkyl acrylate and styrene-butadiene-alkyl methacrylate, styrene-maleic anhydride, styrene-acrylonitrile-methyl acrylate; mixtures of high impact strength from styrene copolymers and another polymer, for example a polyacrylate, a diene polymer or an ethylene-propylene-diene terpolymer; also block copolymers of styrene, for example styrene-butadiene-styrene, styrene-isoprene-styrene, styrene-ethylene/butylene-styrene or styrene-ethylene/propylene-styrene.

Suitable polystyrenes preferably also comprise graft copolymers of styrene or alpha-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylate)s or poly(alkyl methacrylate)s, styrene and acrylonitrile on acrylate-butadiene copolymers, and also their mixtures, as are also known for example as ABS, MBS, ASA or AES polymers.

The polymers preferably comprise polyamides and copolyamides derived from diamines and dicarboxylic acids and/or from aminocarboxylic acids or the corresponding lactams, such as nylon-2,12, nylon-4, nylon-4,6, nylon-6, nylon-6,6, nylon-6,9, nylon-6,10, nylon-6,12, nylon-6,66, nylon-7,7, nylon-8,8, nylon-9,9, nylon-10,9, nylon-10,10, nylon-11, nylon-12, and so on. Such polyamides are known for example under the trade names Nylon®, from DuPont, Ultramid®, from BASF, Akulon® K122, from DSM, Zytel® 7301, from DuPont; Durethan® B 29, from Bayer and Grillamid®, from Ems Chemie.

Also suitable are aromatic polyamides proceeding from m-xylene, diamine and adipic acid; polyamides produced from hexamethylenediamine and iso- and/or terephthalic acid and optionally an elastomer as modifier, for example poly-2,4,4-trimethylhexa-methyleneterephthalamide or poly-m-phenyleneisophthalamide, block copolymers of the aforementioned polyamides with polyolefins, olefin copolymers, ionomers or chemically bonded or grafted elastomers or with polyethers, for example with polyethylene glycol, polypropylene glycol or polytetramethylene glycol. Also EPDM- or ABS-modified polyamides or copolyamides; and also polyamides condensed during processing ("RIM polyamide systems").

The ethylenedialkylphosphinic acid/ester/salts produced as described herein are preferably used in molding compositions further used for producing polymeric moldings.

It is particularly preferable for the flame-retardant molding composition to contain 5% to 30% by weight of ethylenedialkylphosphinic acids, salts or esters produced as described herein, 5% to 85% by weight of polymer or mixtures thereof, 5% to 40% by weight of additives and 5% to 40% by weight of filler, where the sum of the components is always 100% by weight.

The invention also relates to flame retardants containing ethylenedialkylphosphinic acids, salts or esters produced as described herein.

The invention additionally relates to polymer molding compositions, moldings, films, filaments and fibers containing the ethylenedialkylphosphinic salts (III) of the metals Mg, Ca, Al, Zn, Ti, Sn, Zr, Ce or Fe produced in accordance with the invention.

The examples which follow illustrate the invention.

Production, Processing and Testing of
Flame-Retardant Polymer Molding Compositions
and Flame-Retardant Polymer Moldings The flame-retardant components are mixed with the polymer pellets and any additives and incorporated on a twin-screw extruder (model: Leistritz LSM® 30/34) at temperatures of 230 to 260° C. (glassfiber-reinforced PBT) or of 260 to 280° C. (glassfiber-reinforced PA 66). The homogenized polymeric strand was drawn off, cooled in a water bath and then pelletized.

After sufficient drying, the molding compositions were processed on an injection molding machine (Aarburg Allrounder) at melt temperatures of 240 to 270° C. (glassfiber-reinforced PBT) or of 260 to 290° C. (glassfiber-reinforced PA 66) to give test specimens. The test specimens are subsequently flammability tested and classified using the UL 94 (Underwriter Laboratories) test.

UL 94 (Underwriter Laboratories) fire classification was determined on test specimens from each mixture, using test specimens of thickness 1.5 mm.

The UL 94 fire classifications are as follows:

V-0: Afterflame time never longer than 10 sec, total of afterflame times for 10 flame applications not more than 50 sec, no flaming drops, no complete consumption of the specimen, afterglow time for specimens never longer than 30 sec after end of flame application.

V-1: Afterflame time never longer than 30 sec after end of flame application, total of afterflame times for 10 flame applications not more than 250 sec, afterglow time for specimens never longer than 60 sec after end of flame application, other criteria as for V-0.

V-2: Cotton indicator ignited by flaming drops, other criteria as for V-1. Not classifiable (ncl): does not comply with fire classification V-2.

Some specimens examined were also tested for their LOI value. The LOI (Limiting Oxygen Index) value is determined to ISO 4589. According to ISO 4589, the LOI is the lowest oxygen concentration in volume percent which in a mixture of oxygen and nitrogen will support combustion of the plastic. The higher the LOI value, the greater the flammability resistance of the material tested.

| LOI | 23 | flammable |
| LOI | 24-28 | potentially flammable |
| LOI | 29-35 | flame-resistant |
| LOI | >36 | particularly flame-resistant |

Abbreviations of chemicals used

| DM water | demineralized water |
| Deloxan ® THP II | metal scavenger (from Evonik Industries AG) |

EXAMPLE 1

At room temperature, a three-neck flask with stirrer and jacketed coil condenser is initially charged with 580 g of tetrahydrofuran, which is "degassed" by passing nitrogen through for 10 minutes while stirring, and the further operations are executed under nitrogen. 70.0 mg of tris(dibenzylideneacetone)dipalladium and 95.0 mg of 4,5-bis(diphenyl-phosphino)-9,9-dimethylxanthene are added thereto and the mixture is stirred for a further 15 minutes, then 198 g of phosphinic acid in 198 g of water are added and nitrogen is passed through the reaction mixture for 10 minutes. The reaction solution is transferred into a 2 L Büchi reactor and the three-neck flask is rinsed with tetrahydrofuran. While stirring the reaction mixture, the reactor is charged with ethylene to 2.5 bar and the reaction mixture is heated to 80° C. (jacket temperature). After stoichiometric absorption of ethylene, the mixture is cooled to room temperature and free ethylene is discharged by burning it off.

The reaction mixture is freed of the solvent on a rotary evaporator at a maximum of 60° C. and 350-10 mbar. The residue is admixed with 300 g of DM water and stirred at room temperature under a nitrogen atmosphere for 1 hour. The resultant residue is filtered and the filtrate is extracted with 200 mL of toluene. The aqueous phase is freed of the solvent on a rotary evaporator at a maximum of 60° C. and 250-10 mbar.

Yield: 276 g of ethylphosphonous acid (98% of theory).

EXAMPLE 2

At room temperature, a three-neck flask with stirrer and jacketed coil condenser is initially charged with 550 g of butanol, which is degassed by passing nitrogen through while stirring, and the further operations are executed under nitrogen.

Then 73.8 mg of tris(dibenzylideneacetone)dipalladium and 100.2 mg of 4,5-bis(diphenylphosphino)-9,9-dimethylxanthene are added thereto and the mixture is stirred, then 209 g of phosphinic acid in 209 g of water are added. The reaction solution is transferred into a 2 L Büchi reactor which is charged with ethylene to 1 bar while stirring and the reaction mixture is heated to 100° C. After stoichiometric absorption of ethylene, the mixture is cooled and free ethylene is discharged. The reaction mixture is freed of the solvent on a rotary evaporator. 100 g of DM water are added to the residue, the mixture is stirred at room temperature and then filtered, the filtrate is extracted with toluene and freed of the solvent on a rotary evaporator, and the resulting ethylphosphonous acid is collected.

Yield: 295 g (99% of theory).

EXAMPLE 3

At room temperature, a three-neck flask with stirrer and jacketed coil condenser is initially charged with 600 g of acetonitrile, which is degassed by passing nitrogen through while stirring, and the further operations are executed under nitrogen. 53.1 mg of tris(dibenzylideneacetone)dipalladium and 72.1 mg of 4,5-bis(diphenylphosphino)-9,9-dimethylxanthene are added thereto and the mixture is stirred, then 150 g of phosphinic acid in 150 g of toluene are added. The reaction solution is transferred into a 2 L Büchi reactor which is charged with ethylene to 5 bar while stirring and the reaction mixture is heated to 70° C. After stoichiometric absorption of ethylene, the mixture is cooled and free ethylene is discharged. The reaction mixture is freed of the solvent on a rotary evaporator. 100 g of DM water are added to the residue, the mixture is stirred at room temperature and then filtered, the filtrate is extracted with toluene and freed of the solvent on a rotary evaporator, and the resulting ethylphosphonous acid is collected.

Yield: 212 g (99% of theory).

EXAMPLE 4

At room temperature, a three-neck flask with stirrer and jacketed coil condenser is initially charged with 188 g of water, which is degassed by passing nitrogen through while stirring, and the further operations are executed under nitrogen. 0.2 mg of palladium(II) sulfate and 2.3 mg of tris(3-sulfophenyl)phosphine trisodium salt are added thereto and the mixture is stirred, then 66 g of phosphinic acid in 66 g of water are added. The reaction solution is transferred into a 2 L Büchi reactor which is charged with ethylene to 1 bar while stirring and the reaction mixture is heated to 80° C. After stoichiometric absorption of ethylene, the mixture is cooled and free ethylene is discharged. The reaction mixture is freed of the solvent on a rotary evaporator. 100 g of DM water are added to the residue, the mixture is stirred at room temperature and then filtered, the filtrate is extracted with toluene and freed of the solvent on a rotary evaporator, and the resulting ethylphosphonous acid is collected.

Yield: 92 g (98% of theory).

EXAMPLE 5

At room temperature, a three-neck flask with stirrer, thermometer and jacketed coil condenser is initially charged with 188 g of butanol, which is degassed by passing nitrogen through while stirring, and the further operations are executed under nitrogen. 0.2 mg of tris(dibenzylideneacetone)dipalladium and 2.3 mg of 4,5-bis(diphenyl-phosphino)-9,9-dimethylxanthene, 66 g of phosphinic acid in 66 g of water and 117 g of octene are added thereto, and the mixture is stirred. Subsequently, the reaction mixture is heated to 80° C. for 6 h and freed of the solvent on a rotary evaporator. The residue is admixed with 100 g of toluene and extracted with water, then the organic phase is freed from the solvent on a rotary evaporator and the resulting octane-phosphonous acid is collected.

Yield: 176 g (98% of theory).

EXAMPLE 6

As in example 2, 99 g of phosphinic acid, 396 g of butanol, 42 g of ethylene, 6.9 mg of tris(dibenzylideneacetone)dipalladium and 9.5 mg of 4,5-bis(diphenylphosphino)-9,9-dimethylxanthene are converted, then purified by passing through a column filled with Deloxan® THP II, and n-butanol is added once again. At a reaction temperature of 80-110° C., the water formed is removed by azeotropic distillation. The butyl ethylphosphonite product is purified by distillation under reduced pressure.

Yield: 189 g (84% of theory).

EXAMPLE 7

As in example 2, 198 g of phosphinic acid, 198 g of water, 84 g of ethylene, 6.1 mg of palladium(II) sulfate and 25.8 mg of 9,9-dimethyl-4,5-bis(diphenylphosphino)-2,7-sulfonatoxanthene disodium salt are converted, then passed through a column filled with Deloxan® THP II, and then n-butanol is added. At a reaction temperature of 80-110° C., the water formed is removed by azeotropic distillation. The butyl ethylphosphonite product is purified by distillation under reduced pressure.

Yield: 374 g (83% of theory).

EXAMPLE 8

A 500 mL five-neck flask with gas inlet tube, thermometer, jacketed coil condenser and a reflux condenser with gas combustion is initially charged with 94 g (1 mol) of ethylphosphonous acid (prepared as in example 2). At room temperature, ethylene oxide is introduced, a reaction temperature of 70° C. is established and reaction is continued at 80° C. for another hour. The ethylene oxide absorption is 65.7 g. The acid number of the product is less than 1 mg KOH/g. Yield: 129 g (94% of theory) of 2-hydroxyethyl ethylphosphonite as colorless, water-clear product.

EXAMPLE 9

A 1 L 5-neck flask equipped with gas inlet frit, thermometer, stirrer, reflux condenser and UV lamp (0.125 kW, cos φ0.9) is initially charged with 94.0 g of ethylphosphonous acid (prepared as in example 2) in 200 g of acetic acid. At the same time, through the gas inlet frit, about 8 L/h of acetylene are passed through the solution. The reaction temperature is kept at 60° C. by means of a cooling bath. After 8 h, the acetylene stream is closed and the acetylene is removed by passing nitrogen through. The ethylenebis (ethylphosphinic acid) precipitates out in the form of colorless crystals.

Yield: 87 g (81% of theory).

EXAMPLE 10

In a 1 L 5-neck flask equipped with gas inlet frit, thermometer, stirrer, reflux condenser and UV lamp (0.125 kW, cos φ0.9), 94.0 g of ethylphosphonous acid (prepared as in example 2) are dissolved in 200 g of tetrahydrofuran.

At the same time, through the gas inlet frit, about 8 L/h of acetylene are passed through the solution. The reaction temperature is kept at 40° C. by means of a cooling bath. After 8 h, the acetylene stream is closed and the acetylene is removed by passing nitrogen through. The ethylenebis (ethylphosphinic acid) precipitates out in the form of colorless crystals.

Yield: 79 g (74% of theory).

EXAMPLE 11

A 1 L 5-neck flask equipped with gas inlet frit, thermometer, stirrer, reflux condenser and UV lamp (0.125 kW, cos φ0.9) is initially charged with 94.0 g of ethylphosphonous acid (prepared as in example 2) in 200 g of acetonitrile.

At the same time, through the gas inlet frit, about 10 L/h of acetylene are passed through the solution. The reaction temperature is kept at 50° C. by means of a cooling bath. After 6 h, the acetylene stream is closed. The ethylenebis (ethylphosphinic acid) precipitates out in the form of colorless crystals. These are filtered off.

Yield: 92 g (86% of theory).

EXAMPLE 12

In a 1 L 5-neck flask equipped with gas inlet frit, thermometer, stirrer, reflux condenser and UV lamp (0.125 kW, cos φ0.9), 94.0 g of ethylphosphonous acid (prepared as in example 2) are dissolved in 200 g of water.

At the same time, through the gas inlet frit, about 15 L/h of acetylene are passed through the solution for 5 h. The reaction temperature is kept at 30° C. by means of a cooling bath. The ethylenebis(ethylphosphinic acid) precipitates out in the form of colorless crystals. These are filtered off.

Yield: 83 g (78% of theory).

EXAMPLE 13

A 2 L Büchi autoclave equipped with gas inlet frit, thermometer, stirrer and UV lamp (0.125 kW, cos φ0.9) is initially charged with 94.0 g of ethylphosphonous acid (prepared as in example 2) in 400 g of acetonitrile and pressurized with acetylene to 3 bar. The reaction temperature is kept at 50° C. by means of the water cooling. After 6 h, the reaction is ended. The ethylenebis(ethylphosphinic acid) precipitates out in the form of colorless crystals. These are filtered off.

Yield: 95 g (89% of theory).

EXAMPLE 14

A 2 L Büchi autoclave equipped with gas inlet frit, thermometer, stirrer and UV lamp (0.125 kW, cos φ0.9) is initially charged with 94.0 g of ethylphosphonous acid (prepared as in example 2) in 350 g of water and pressurized with acetylene to 1.2 bar. The reaction temperature is kept at 60° C. by means of the water cooling. After 8 h, the reaction is ended. The ethylenebis(ethylphosphinic acid) precipitates out in the form of colorless crystals, which are filtered off.

Yield: 88 g (82% of theory).

EXAMPLE 15

A 2 L Büchi autoclave equipped with gas inlet frit, thermometer, stirrer and UV lamp (0.125 kW, cos φ0.9) is initially charged with 94.0 g of ethylphosphonous acid (prepared as in example 2) in 300 g of butanol and pressurized with acetylene to 2 bar. The reaction temperature is kept at 80° C. by means of the water cooling. After 4 h, the reaction is ended. The ethylenebis(ethylphosphinic acid) precipitates out in the form of colorless crystals. These are filtered off.

Yield: 94 g (88% of theory).

EXAMPLE 16

In a 1 L 5-neck flask equipped with gas inlet frit, thermometer, stirrer, reflux condenser and UV lamp (0.125 kW, cos φ0.9), 99.0 g of ethylphosphonous acid (prepared as in example 2) are dissolved in 250 g of butanol.

At the same time, through the gas inlet frit, about 1 L/h of acetylene is passed through the solution for 15 h. The reaction temperature is kept at 80° C. by means of a cooling bath. The ethylenebis(ethylphosphinic acid) precipitates out in the form of colorless crystals. These are filtered off and washed with butanol.

Yield: 79 g (70% of theory).

EXAMPLE 17

In a 1 L 5-neck flask equipped with gas inlet frit, thermometer, stirrer, reflux condenser and UV lamp (0.125 kW, cos φ0.9), 122 g of octanephosphonous acid (prepared as in example 3) are dissolved in 250 g of butanol.

At the same time, through the gas inlet frit, about 8 L/h of acetylene are passed through the solution for 5 h. The reaction temperature is kept at 60° C. by means of a cooling bath. After removal of the solvent on a rotary evaporator and extraction with toluene, the ethylenebis(octylphosphinic acid) is obtained in a yield of 59 g (81% of theory).

EXAMPLE 18

321 g (1.5 mol) of ethylenebis(ethylphosphinic acid) (prepared as in example 11) are dissolved at 85° C. in 400 mL of toluene, and 888 g (12 mol) of butanol are added. At a reaction temperature of about 100° C., the water formed is removed by azeotropic distillation. After purification by chromatography, 401 g (83% of theory) of ethylenebis (ethylphosphinic acid butyl ester) are obtained.

EXAMPLE 19

321 g (1.5 mol) of ethylenebis(ethylphosphinic acid) (prepared as in example 11) are dissolved at 85° C. in 400 mL of toluene, 409 g (6.6 mol) of ethylene glycol are added and esterification is effected in a distillation apparatus with a water separator at about 100° C. over 4 h. After the esterification has ended, the toluene and excess ethylene glycol are removed under reduced pressure. 448 g (99% of theory) of ethylenebis(ethylphosphinic acid 2-hydroxyethyl ester) are obtained as a colorless oil.

EXAMPLE 20

To 326 g (1 mol) of ethylenebis(ethylphosphinic acid butyl ester) (prepared according to example 16) are added 155 g (2.5 mol) of ethylene glycol and 0.4 g of potassium titanyloxalate, and the mixture is stirred at 200° C. for 2 h. By gradual evacuation, volatile components are distilled off. 296 g (98% of theory) of ethylenebis(ethylphosphinic acid 2-hydroxyethyl ester) are obtained.

EXAMPLE 21

A 500 mL five-neck flask with gas inlet tube, thermometer, jacketed coil condenser and reflux condenser with gas combustion is initially charged with 214 g (1 mol) of ethylenebis(ethylphosphinic acid), prepared as in example 11. At room temperature, ethylene oxide is introduced. While cooling, a reaction temperature of 70° C. is established and reaction is continued at 80° C. for another hour. The ethylene oxide absorption is 64.8 g. The acid number of the product is less than 1 mg KOH/g. 257 g (95% of theory) of ethylenebis(ethylphosphinic acid 2-hydroxyethyl ester) are obtained as a colorless, water-clear liquid.

EXAMPLE 22

642 g (3 mol) of ethylenebis(ethylphosphinic acid) (prepared as in example 11) are dissolved in 860 g of water and initially charged in a 5 L five-neck flask with thermometer, reflux condenser, jacketed coil condenser and dropping funnel and neutralized with about 960 g (12 mol) of 50% sodium hydroxide solution. At 85° C., a mixture of 2583 g of a 46% aqueous solution of $Al_2(SO_4)_3 \cdot 14H_2O$ is added. Subsequently, the solid obtained is filtered off, washed with hot water and dried at 130° C. under reduced pressure. Yield: 642 g (93% of theory) of colorless ethylenebis(ethylphosphinic acid) aluminum(III) salt.

EXAMPLE 23

214 g (1 mol) of ethylenebis(ethylphosphinic acid) (prepared as in example 11) and 170 g of titanium tetrabutoxide are heated under reflux in 500 mL of toluene for 40 hours. Butanol formed is distilled off from time to time with portions of toluene. The solution formed is subsequently freed of the solvent. This gives 229 g of ethylenebis(ethylphosphinic acid) titanium salt.

Use examples:

EXAMPLE 24

To 39.1 g of ethylenebis(ethylphosphinic acid 2-hydroxyethyl ester), prepared as in example 18, are added 290 g of terephthalic acid, 188 g of ethylene glycol and 0.34 g of zinc acetate, and the mixture is heated to 200° C. for 2 h. Then 0.29 g of trisodium phosphate anhydrate and 0.14 g of antimony(III) oxide are added, and the mixture is heated to 280° C. and then evacuated. Specimens of thickness 1.6 mm are then produced by injection molding from the resulting melt (363 g, phosphorus content: 2.2%) for the measurement of the oxygen index (LOI) to ISO 4589-2 and for the UL 94 fire test (Underwriter Laboratories). The specimens thus produced gave an LOI of 42 and achieved UL 94 fire class V-0. Corresponding specimens without ethylenebis(ethylphosphinic acid 2-hydroxyethyl ester) gave an LOI of only 31 and achieved only UL 94 fire class V-2.

The polyester molding containing ethylenebis(ethylphosphinic acid 2-hydroxyethyl ester) thus clearly exhibits very good flame-retardant properties.

EXAMPLE 25

To 19.6 g of ethylenebis(ethylphosphinic acid), prepared analogously to example 11, are added 12.9 g of 1,3-propylene glycol, and the water formed in the esterification is drawn off at 160° C. Then 378 g of dimethyl terephthalate, 192 g of 1,3-propanediol, 0.22 g of tetrabutyl titanate and 0.05 g of lithium acetate are added and the mixture is heated to 130 to 180° C. while stirring for 2 h, then under reduced pressure to 270° C. The polymer (418 g) contains 1.4% phosphorus; the LOI is 38.

EXAMPLE 26

To 19.7 g of ethylenebis(ethylphosphinic acid) (prepared as in example 11) are added 367 g of dimethyl terephthalate, 238 g of 1,4-butanediol, 0.22 g of tetrabutyl titanate and 0.05 g of lithium acetate, and the mixture is heated to 130 to 180° C. while stirring for 2 h, then under reduced pressure to 270° C. The polymer (432 g) contains 1.3% phosphorus; the LOI is 34, whereas that of untreated polybutylene terephthalate is only 23.

EXAMPLE 27

In a 250 mL five-neck flask with reflux condenser, stirrer, thermometer and nitrogen inlet, 100 g of a bisphenol A bisglycidyl ether having an epoxy value of 0.55 mol/100 g (Beckopox EP 140, from Solutia) and 13.9 g (0.13 mol) of ethylenebis(ethylphosphinic acid) (prepared analogously to example 11) are heated to a maximum of 150° C. while stirring. After 30 min, a clear melt is obtained. After stirring at 150° C. for a further hour, the melt is cooled and crushed with a mortar and pestle. This gives 117.7 g of a white powder having a phosphorus content of 3.5%.

EXAMPLE 28

In a 2 L flask with stirrer, water separator, thermometer, reflux condenser and nitrogen inlet, 29.4 g of phthalic anhydride, 19.6 g of maleic anhydride, 24.8 g of propylene glycol, 20.4 g of ethylenebis(ethylphosphinic acid 2-hydroxyethyl ester) (prepared as in example 18), 20 g of xylene and 50 mg of hydroquinone are heated to 100° C. while stirring and passing nitrogen through. When the exothermic reaction sets in, the heating is removed. After the reaction has abated, stirring is continued at about 190° C. After 14 g of water have separated out, the xylene is distilled off and the polymer melt is cooled. This gives 86.2 g of a white powder having a phosphorus content of 4.8%.

EXAMPLE 29

A mixture of 50% by weight of polybutylene terephthalate, 20% by weight of 3-ethylenebis(ethylphosphinic acid) aluminum(III) salt (prepared as in example 20) and 30% by weight of glass fibers is compounded in a twin-screw extruder (model: Leistritz LSM 30/34) at temperatures of 230 to 260° C. to give a polymer molding composition. The homogenized polymer strand is drawn off, cooled in a water bath and then pelletized. After drying, the molding compositions are processed in an injection molding machine (model: Aarburg Allrounder) at 240 to 270° C. to give polymer moldings and a UL-94 classification of V-0 is determined.

EXAMPLE 30

A mixture of 53% by weight of nylon-6,6, 30% by weight of glass fibers and 17% by weight of 3-ethylenebis(ethylphosphinic acid) titanium salt (prepared as in example 21) is compounded in a twin-screw extruder (model: Leistritz LSM 30/34) to give polymer molding compositions. The homogenized polymer strand is drawn off, cooled in a water bath and then pelletized. After drying, the molding materials are processed in an injection molding machine (model: Aarburg Allrounder) at 260 to 290° C. to give polymer moldings, and a UL-94 classification of V-0 is obtained.

The epoxy resin formulations described further up were used to produce polymer moldings. For this purpose, the individual components are weighed out and mixed with one another in a suitable vessel at high stirrer speed. Room temperature solid resins are melted beforehand. After mixing, the resin mixture is devolatilized by applying reduced pressure.

The finished resin mixture is introduced into a suitable casting mold and hardened at room temperature or in a drying cabinet. The thickness of the polymer moldings produced was 3 mm or 1.6 mm.

In addition to the flammability class according to UL 94, the Charpy impact resistance (DIN EN ISO 179-1) and the hydrolysis stability were preferably tested on the polymer moldings produced.

To determine the hydrolysis stability, polymer moldings were stored in each case at 100° C. in 80 mL of water for 24 h. After storage, the phosphorus content of the water was determined.

In the studies conducted, it was found that the ethylenediethylphosphinic acid prepared in accordance with the invention, in addition to very good flame-retardant action, also reduces the brittleness of the hardened epoxy resin matrix, and is not hydrolyzed in the course of water storage.

The result is explained hereinafter by additional examples:

To produce the flame-retardant epoxy resin formulations, the following compounds were used:
Beckopox® EP 140 (BPA-EP resin, Solutia, United States)
PF® 0790 K04 (phenol novolac, Hexion Chemical, United States)
2-Phenylimidazole (Degussa/Trostberg, Germany)
TS®-601 (aluminum trihydroxide, Martinswerk, Germany)
DOPO®-HQ (10-(2,5-dihydroxyphenyl)-10H-9-oxa-10-phospha-phenanthrene 10-oxide, Sanko Co., Ltd., Japan)

EXAMPLE 31 a) Preparation of a Phosphorus-Modified Epoxy Resin Based on Ethylenediethylphosphinic Acid A four-neck flask equipped with reflux condenser, thermocouple, nitrogen inlet and stirrer is initially charged with 100 g of Beckopox® EP 140, EP value 180 g/mol. While stirring, the mixture is heated to 110° C. and residual water is removed under reduced pressure, followed by ventilation with dry nitrogen. Thereafter, the temperature in the flask is increased to 130° C., and 11.7 g of ethanebisethylphosphinic acid are added while stirring with nitrogen flow. The temperature of the reaction mixture is increased to 160° C. and maintained for 1 h. The product is subsequently poured out while hot and cooled. This gave a phosphorus-modified epoxy resin with a phosphorus content of 3% by weight and an epoxy equivalent of 267 g/mol.

The proportion of phosphorus in the epoxy resin was varied correspondingly by means of different amounts of ethanebisethylphosphinic acid prepared in accordance with the invention in the synthesis (examples 31 a) 1 to a) 4).

b) Preparation of a Phosphorus-Modified Epoxy Resin Based on DOPO-HQ (Comparative Example, 31 b))

A four-neck flask equipped with reflux condenser, thermocouple, nitrogen inlet and stirrer is initially charged with 100 g of Beckopox® EP 140, EP value 180 g/mol. While stirring, the mixture is heated to 110° C. and residual water is removed under reduced pressure, followed by ventilation with dry nitrogen. Thereafter, the temperature in the flask is increased to 130° C., and 19 g of DOPO-HQ are added while stirring with nitrogen flow. The temperature of the reaction mixture is increased to 160° C. and kept there for 2.5 h. The product is subsequently poured out while hot and cooled.

A phosphorus-modified epoxy resin with a phosphorus content of 1.5% by weight and an epoxy equivalent of 286 g/mol was obtained.

Table 1 shows the combination of the ethanebisethylphosphinic acid prepared in accordance with the invention with a bisphenol A novolac as a hardener and in an example with an additional flame retardant. The accelerator used was 2-phenylimidazole.

As can be inferred from table 1, at a concentration of in the P resin, a V-0 classification was attained both at thickness 3 mm and at 1.6 mm. The impact resistances of the polymer moldings produced with these formulations were always at a higher level compared to the reference example. In the water used for the hydrolysis, moreover, no phosphorus was found. Accordingly, the ethanebisethylphosphinic acid prepared in accordance with the invention is not hydrolyzed and is not then washed out of the thermoset network in the course of water storage.

This has the advantage that the phosphorus compound of the invention remains in the product, i.e. the polymer, and hence, advantageously, high product stability, longer-lasting material properties and also no "exudation" are achieved.

EXAMPLE 32 (COMPARATIVE EXAMPLE FOR PREPARATION OF ETHYLENEBIS(ETHYLPHOSPHINIC ACID))

In a 1 L 5-neck flask equipped with gas inlet frit, thermometer, stirrer, reflux condenser and initiator metering system, a solution of 94.0 g of ethylphosphonous acid (prepared as in example 1) is dissolved in 200 g of glacial acetic acid and heated to about 90° C. While stirring, a solution of 11.4 g of sodium peroxodisulfate in 30 g of water is metered in over a period of 5 h. At the same time, through the gas inlet frit, about 10 L/h of acetylene are passed through the solution. In the course of this, the reaction temperature is kept at about 100° C. After the acetylene has been removed by passing nitrogen through, the mixture is left to cool, in the course of which ethylenebis(ethyl-phosphinic acid) precipitates out in the form of colorless crystals. The product contains, as well as ethylenebis(ethylphosphinic acid), also 7% ethylphosphonic acid as oxidative by-product as a result of the use of the free-radical peroxide initiator.

After washing with acetic acid, ethylenebis(ethylphosphinic acid) product is obtained in a yield of 86.7 g (81% of theory).

TABLE 1

|  |  | Example 31 | | | | |
| --- | --- | --- | --- | --- | --- | --- |
|  |  | a) 1 | a) 2 | a) 3 | a) 4 | b) (C)* |
| Resin formulation | P-modified EP resin based on ethanebis(ethyl-phosphinic acid) | 100 | 100 | 100 | 100 | — |
|  | P-modified EP resin based on DOPO-HQ | — | — | — | — | 100 |
|  | Phenol novolac | 34 | 43 | 46 | 46 | 37 |
|  | 2-Phenylimidazole | 0.03 | 0.03 | 0.03 | 0.03 | 0.03 |
|  | Aluminum trihydroxide (TS601) | — | — | — | 25 | — |
| Properties of the polymer molding | P content in test plaque [%] | 2.6 | 1.8 | 1.3 | 1.3 | 1.1 |
|  | Charpy impact resistance [kJ/cm2] | 50 | 44 | 35 | 30 | 26 |
|  | P content of water after storage at 100° C. [ppm] | <1 | <1 | <1 | <1 | <1 |
|  | UL 94 | V0 | V0 | V1 | V0 | V0 |

*(C) = comparative example

The washed end product also still contains secondary components and impurities which are attributable to the free-radical initiator and still have to be removed. Secondary components of this kind are, for example, the decomposition products of the free-radical initiator, but also the solvent in which the free-radical initiator is dissolved. Accordingly, these by-products and decomposition products are also introduced into the polymer with the ethylenebis(ethylphosphinic acid) prepared only by free-radical means, and lead to higher instability of the polymer. Moreover, the handling of free-radical initiators in the laboratory and on the production scale is inconvenient and costly because of the high thermal instability in some cases.

The invention claimed is:

1. A process for preparing ethylenedialkylphosphinic acids, esters and salts, comprising the steps of:
a) reacting a phosphinic acid source (I)

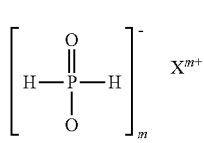

(I)

with olefins (IV)

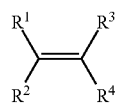

(IV)

in the presence of a catalyst A at a temperature of 60-100° C. to give an alkylphosphonous acid (II), or salt or ester thereof

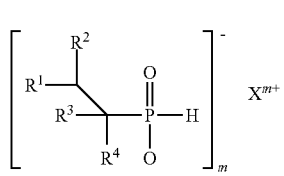

(II)

b) reacting the alkylphosphonous acid (II), or salt or ester thereof, thus formed with an acetylenic compound (V)

(V)

in the presence of a catalyst B at a temperature of 50-80° C. to give the ethylenedialkylphosphinic acid derivative (III)

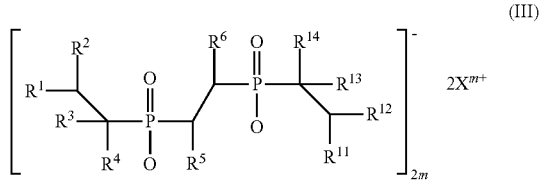

(III)

wherein
$R^1$, $R^2$, $R^3$, $R^4$, $R^5$, $R^6$, $R^{11}$, $R^{12}$, $R^{13}$, and $R^{14}$ are the same or different and are each independently H, $C_1$-$C_{18}$-alkyl or phenyl, where the phenyl is optionally substituted by C(O)CH$_3$, OH, CH$_2$OH, NH$_2$, NO$_2$, OCH$_3$, SH and/or OC(O)CH$_3$, and X is H, Ca, Mg, Al, Zn, Ti, Ce, Fe, methyl, ethyl, n-propyl, isopropyl, n-butyl, isobutyl, tert-butyl, phenyl, poly(oxyethylene), oxypropylene, poly(oxypropylene), oxybutylene, poly(oxybutylene, allyl ether, a protonated nitrogen base of a combination thereof,
m is 1 to 4,
the catalyst A is selected from the group consisting of transition metals, transition metal compounds, catalyst systems composed of a transition metal and/or a transition metal compound and at least one ligand and a combination thereof, and
the catalyst B is UV radiation having a wavelength between 400 and 10 nm.

2. The process as claimed in claim 1, wherein the alkylphosphonous acid (II), or salt or ester thereof, obtained after step a) is esterified with an alkene oxide or an alcohol, and the alkylphosphonous ester (II) and/or ethylenedialkylphosphinic ester (III) formed is subjected to the reaction step b).

3. The process as claimed in claim 1, wherein the ethylenedialkylphosphinic acid (III), or salt or ester thereof, obtained after step b) is esterified with an alkene oxide or an alcohol M-OH and/or M'-OH, wherein the alcohol M-OH is a linear or branched, saturated or unsaturated, monohydric alcohol and the alcohol M'-OH is a polyhydric organic alcohol each having a carbon chain length of $C_1$-$C_{18}$.

4. The process as claimed in claim 1, wherein the ethylenedialkylphosphinic acid (III), or salt or ester thereof, obtained after step b) is subsequently reacted, in a step c), with metal compounds of Mg, Ca, Al, Ti, Fe, Zn, Ce, a protonated nitrogen base or a combination thereof to give the corresponding ethylenedialkylphosphinic salts (III) of these metals and/or of a nitrogen compound.

5. The process as claimed in claim 1, wherein $R^1$, $R^2$, $R^3$, $R^4$, $R^5$, $R^6$, $R^{11}$, $R^{12}$, $R^{13}$ and $R^{14}$ are the same or different and are each independently H, methyl, ethyl, n-propyl, isopropyl, n-butyl, isobutyl, tert-butyl or phenyl.

6. The process as claimed in claim 1, wherein the transition metals are rhodium, nickel, palladium, platinum, ruthenium or a combination thereof.

7. The process as claimed in claim 1, wherein gaseous olefins are used.

8. The process as claimed in claim 7, wherein the gaseous olefins are ethylene, propylene, 1-butene, 2-butene, 2-methylpropylene or a combination thereof.

9. The process as claimed in claim 1, wherein the pressure in each of reaction step a) and reaction step b) is 0-10 bar.

10. The process as claimed in claim 1, wherein the pressure in each of reaction step a) and reaction step b) is 1-5 bar and gas flow in each of reaction step a) and reaction step b) is 5-12 L/h.

11. The process as claimed in claim 1, wherein the acetylenic compound (V) is acetylene, methylacetylene, 1-butyne, 1-hexyne, 2-hexyne, 1-octyne, 4-octyne, 1-butyn-4-ol, 2-butyn-1-ol, 3-butyn-1-ol, 5-hexyn-1-ol, 1-octyn-3-ol, 1-pentyne, phenylacetylene, trimethylsilylacetylene or a combination thereof.

12. The process as claimed in claim 1, wherein the acetylenic compound (V) is acetylene.

* * * * *